US008603180B2

(12) United States Patent
White et al.

(10) Patent No.: US 8,603,180 B2
(45) Date of Patent: Dec. 10, 2013

(54) PATIENT-SPECIFIC ACETABULAR ALIGNMENT GUIDES

(75) Inventors: John R. White, Winona Lake, IN (US); Lance D. Perry, Warsaw, IN (US); Aaron P. Smith, Warsaw, IN (US); Jason D. Meridew, Warsaw, IN (US); Bryan Morrison, Goshen, IN (US); W Jason Slone, Silver Lake, IN (US); Tyler D. Witt, Fond du Lac, WI (US); Mark A. Bollinger, Fort Wayne, IN (US); Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/111,007

(22) Filed: May 19, 2011

(65) Prior Publication Data
US 2011/0224674 A1 Sep. 15, 2011

Related U.S. Application Data

(63) Continuation-in-part of application No. 13/041,469, filed on Mar. 7, 2011, and a continuation-in-part of application No. 13/041,495, filed on Mar. 7, 2011, and a continuation-in-part of application No. 13/041,665, filed on Mar. 7, 2011, and a continuation-in-part of application No. 13/041,883, filed on Mar. 7, 2011, which is a continuation-in-part of application No. 12/978,069, filed on Dec. 23, 2010, which is a
(Continued)

(51) Int. Cl.
*A61B 17/88* (2006.01)
(52) U.S. Cl.
USPC .......................... 623/22.11; 606/91

(58) Field of Classification Search
USPC ........................... 623/21.18–22.21
See application file for complete search history.

(56) References Cited

U.S. PATENT DOCUMENTS

| 1,480,285 A | 1/1924 | Moore |
| 2,181,746 A | 11/1939 | Siebrandt |

(Continued)

FOREIGN PATENT DOCUMENTS

| CA | 2447694 A1 | 12/2002 |
| CA | 2501041 A1 | 4/2004 |

(Continued)

OTHER PUBLICATIONS

"Amazing Precision. Beautiful Results. The next evolution of MAKOplasty® is here," brochure. (Feb. 2009) MAKO Surgical Corp. 6 pages.

(Continued)

*Primary Examiner* — David Isabella
*Assistant Examiner* — Ann Schillinger
(74) *Attorney, Agent, or Firm* — Harness, Dickey

(57) ABSTRACT

An acetabular device includes a patient-specific acetabular alignment guide including a bone engagement surface. The bone engagement surface has a first portion configured and shaped to be conforming and complementary to an acetabular rim surface and a second portion configured and shaped to be conforming and complementary to a periacetabular area of an acetabulum of a patient. The acetabular alignment guide includes a plurality of guiding formations extending through the second portion for guiding a plurality of alignment pins therethrough. The bone engagement surface and the plurality of guiding formations are prepared from a three-dimensional model of the acetabulum of the specific patient reconstructed pre-operatively from a scan of the patient.

17 Claims, 19 Drawing Sheets

Related U.S. Application Data continuation-in-part of application No. 12/973,214, filed on Dec. 20, 2010, which is a continuation-in-part of application No. 12/955,361, filed on Nov. 29, 2010, which is a continuation-in-part of application No. 12/938,913, filed on Nov. 3, 2010, and a continuation-in-part of application No. 12/938,905, filed on Nov. 3, 2010, which is a continuation-in-part of application No. 12/893,306, filed on Sep. 29, 2010, which is a continuation-in-part of application No. 12/888,005, filed on Sep. 22, 2010, now Pat. No. 8,377,066, which is a continuation-in-part of application No. 12/714,023, filed on Feb. 26, 2010, now Pat. No. 8,241,293, which is a continuation-in-part of application No. 12/571,969, filed on Oct. 1, 2009, which is a continuation-in-part of application No. 12/486,992, filed on Jun. 18, 2009, and a continuation-in-part of application No. 12/389,901,filed on Feb. 20, 2009, now Pat. No. 8,133,234, which is a continuation-in-part of application No. 12/211,407, filed on Sep. 16, 2008, which is a continuation-in-part of application No. 12/039,849, filed on Feb. 29, 2008, now Pat. No. 8,282,646, and a continuation-in-part of application No. 11/756,057, filed on May 31, 2007, now Pat. No. 8,092,465, said application No. 12/039,849 is a continuation-in-part of application No. 11/971,390, filed on Jan. 9, 2008, now Pat. No. 8,070,752, which is a continuation-in-part of application No. 11/363,548, filed on Feb. 27, 2006, now Pat. No. 7,780,672, said application No. 12/039,849 is a continuation-in-part of application No. 12/025,414, filed on Feb. 4, 2008, now Pat. No. 8,298,237, said application No. 13/111,007 is a continuation-in-part of application No. 12/872,663, filed on Aug. 31, 2010, now Pat. No. 8,407,067, said application No. 13/111,007 is a continuation-in-part of application No. 12/483,807, filed on Jun. 12, 2009, now Pat. No. 8,473,305, which is a continuation-in-part of application No. 12/371,096, filed on Feb. 13, 2009, which is a continuation-in-part of application No. 12/103,824, filed on Apr. 16, 2008, now abandoned, said application No. 13/111,007 is a continuation-in-part of application No. 12/103,834, filed on Apr. 16, 2008, now Pat. No. 7,967,868.

(60) Provisional application No. 61/446,660, filed on Feb. 25, 2011, provisional application No. 60/953,620, filed on Aug. 2, 2007, provisional application No. 60/947,813, filed on Jul. 3, 2007, provisional application No. 60/911,297, filed on Apr. 12, 2007, provisional application No. 60/892,349, filed on Mar. 1, 2007, provisional application No. 60/812,694, filed on Jun. 9, 2006, provisional application No. 60/953,637, filed on Aug. 2, 2007, provisional application No. 61/310,752, filed on Mar. 5, 2010, provisional application No. 60/912,178, filed on Apr. 17, 2007.

(56) References Cited

U.S. PATENT DOCUMENTS

| | | | |
|---|---|---|---|
| 2,407,845 | A | 9/1946 | Nemeyer |
| 2,618,913 | A | 11/1952 | Plancon et al. |
| 2,910,978 | A | 11/1959 | Urist |
| 3,840,904 | A | 10/1974 | Tronzo |
| 4,246,895 | A | 1/1981 | Rehder |
| 4,306,866 | A | 12/1981 | Weissman |
| 4,324,006 | A | 4/1982 | Charnley |
| 4,421,112 | A | 12/1983 | Mains et al. |
| 4,436,684 | A | 3/1984 | White |
| 4,475,549 | A | 10/1984 | Oh |
| 4,506,393 | A | 3/1985 | Murphy |
| 4,524,766 | A | 6/1985 | Petersen |
| 4,528,980 | A * | 7/1985 | Kenna .......................... 606/80 |
| 4,619,658 | A | 10/1986 | Pappas et al. |
| 4,621,630 | A | 11/1986 | Kenna |
| 4,632,111 | A | 12/1986 | Roche |
| 4,633,862 | A | 1/1987 | Petersen |
| 4,663,720 | A | 5/1987 | Duret et al. |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,719,907 | A | 1/1988 | Banko et al. |
| 4,721,104 | A | 1/1988 | Kaufman et al. |
| 4,722,330 | A | 2/1988 | Russell et al. |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A | 1/1990 | Vandewalls |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A | 4/1991 | Woolson |
| 5,019,105 | A | 5/1991 | Wiley |
| 5,030,221 | A | 7/1991 | Buechel et al. |
| 5,041,117 | A | 8/1991 | Engelhardt |
| 5,053,037 | A | 10/1991 | Lackey |
| 5,053,039 | A | 10/1991 | Hofmann et al. |
| 5,086,401 | A | 2/1992 | Glassman et al. |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A | 6/1992 | Bert et al. |
| 5,129,908 | A | 7/1992 | Petersen |
| 5,129,909 | A | 7/1992 | Sutherland |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,176,711 | A | 1/1993 | Grimes |
| 5,246,444 | A | 9/1993 | Schreiber |
| 5,258,032 | A | 11/1993 | Bertin |
| 5,261,915 | A | 11/1993 | Durlacher et al. |
| 5,274,565 | A | 12/1993 | Reuben |
| 5,299,288 | A | 3/1994 | Glassman et al. |
| 5,300,077 | A | 4/1994 | Howell |
| 5,320,625 | A | 6/1994 | Bertin |
| 5,342,366 | A | 8/1994 | Whiteside et al. |
| 5,344,423 | A | 9/1994 | Dietz et al. |
| 5,360,446 | A | 11/1994 | Kennedy |
| 5,364,402 | A | 11/1994 | Mumme et al. |
| 5,368,858 | A | 11/1994 | Hunziker |
| 5,370,692 | A | 12/1994 | Fink et al. |
| 5,370,699 | A | 12/1994 | Hood et al. |
| 5,405,395 | A | 4/1995 | Coates |
| 5,408,409 | A | 4/1995 | Glassman et al. |
| 5,415,662 | A | 5/1995 | Ferrante et al. |
| 5,417,694 | A | 5/1995 | Marik et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |

| Patent No. | Date | Inventor |
|---|---|---|
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,671,018 A | 9/1997 | Ohara et al. |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,925,077 A | 7/1999 | Williamson et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,132,469 A | 10/2000 | Schroeder |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |
| 6,416,553 B1 | 7/2002 | White et al. |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,682,567 B1 | 1/2004 | Schroeder |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,990,220 B2 | 1/2006 | Ellis et al. |
| 7,029,479 B2 | 4/2006 | Tallarida et al. |
| 7,042,222 B2 | 5/2006 | Zheng et al. |

| | | |
|---|---|---|
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,207 B1 | 2/2008 | Smith |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,211,112 B2 | 7/2012 | Novak et al. |
| 8,241,292 B2 | 8/2012 | Collazo |
| 8,241,293 B2 | 8/2012 | Stone et al. |
| 8,265,790 B2 | 9/2012 | Amiot et al. |
| 8,282,646 B2 | 10/2012 | Schoenefeld et al. |
| 8,298,237 B2 | 10/2012 | Schoenefeld et al. |
| 8,303,596 B2 | 11/2012 | Plaβky et al. |
| 8,333,772 B2 | 12/2012 | Fox et al. |
| 8,355,773 B2 | 1/2013 | Leitner et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0120342 A1 | 8/2002 | Gibbs |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1* | 7/2003 | McMinn .................... 623/23.14 |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0212459 A1 | 11/2003 | Gibbs |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |

| | | |
|---|---|---|
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0225369 A1 | 11/2004 | Lakin et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0021148 A1 | 1/2005 | Gibbs |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106391 A1 | 5/2007 | Ronk |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |

| | | | | | | |
|---|---|---|---|---|---|---|
| 2008/0009952 A1 | 1/2008 | Hodge | | 2009/0088759 A1 | 4/2009 | Aram et al. |
| 2008/0015599 A1 | 1/2008 | D'Alessio et al. | | 2009/0088760 A1 | 4/2009 | Aram et al. |
| 2008/0015603 A1 | 1/2008 | Collazo | | 2009/0088761 A1 | 4/2009 | Roose et al. |
| 2008/0015604 A1 | 1/2008 | Collazo | | 2009/0088763 A1 | 4/2009 | Aram et al. |
| 2008/0015605 A1 | 1/2008 | Collazo | | 2009/0088865 A1 | 4/2009 | Brehm |
| 2008/0021299 A1 | 1/2008 | Meulink | | 2009/0088866 A1 | 4/2009 | Case |
| 2008/0021494 A1 | 1/2008 | Schmelzeisen-Redeker et al. | | 2009/0089034 A1 | 4/2009 | Penney et al. |
| 2008/0021567 A1 | 1/2008 | Meulink et al. | | 2009/0089081 A1 | 4/2009 | Haddad |
| 2008/0027563 A1 | 1/2008 | Johnson et al. | | 2009/0093815 A1 | 4/2009 | Fletcher et al. |
| 2008/0033442 A1 | 2/2008 | Amiot et al. | | 2009/0093816 A1 | 4/2009 | Roose et al. |
| 2008/0039850 A1 | 2/2008 | Rowley et al. | | 2009/0096613 A1 | 4/2009 | Westrick |
| 2008/0051799 A1 | 2/2008 | Bonutti | | 2009/0099567 A1 | 4/2009 | Zajac |
| 2008/0051910 A1 | 2/2008 | Kammerzell et al. | | 2009/0105837 A1 | 4/2009 | Lafosse et al. |
| 2008/0058945 A1 | 3/2008 | Hajaj et al. | | 2009/0118736 A1 | 5/2009 | Kreuzer |
| 2008/0058947 A1 | 3/2008 | Earl et al. | | 2009/0118769 A1 | 5/2009 | Sixto, Jr. et al. |
| 2008/0062183 A1 | 3/2008 | Swaelens | | 2009/0131941 A1 | 5/2009 | Park et al. |
| 2008/0065225 A1 | 3/2008 | Wasielewski et al. | | 2009/0131942 A1 | 5/2009 | Aker et al. |
| 2008/0097451 A1 | 4/2008 | Chen et al. | | 2009/0138020 A1 | 5/2009 | Park et al. |
| 2008/0112996 A1 | 5/2008 | Harlow et al. | | 2009/0149965 A1 | 6/2009 | Quaid |
| 2008/0114370 A1 | 5/2008 | Schoenefeld | | 2009/0149977 A1 | 6/2009 | Schendel |
| 2008/0133022 A1 | 6/2008 | Caylor | | 2009/0151736 A1 | 6/2009 | Belcher et al. |
| 2008/0140081 A1 | 6/2008 | Heavener et al. | | 2009/0157083 A1 | 6/2009 | Park et al. |
| 2008/0140209 A1 | 6/2008 | Iannotti et al. | | 2009/0163922 A1 | 6/2009 | Meridew et al. |
| 2008/0140213 A1 | 6/2008 | Ammann et al. | | 2009/0163923 A1 | 6/2009 | Flett et al. |
| 2008/0146969 A1 | 6/2008 | Kurtz | | 2009/0164024 A1 | 6/2009 | Rudan et al. |
| 2008/0147072 A1 | 6/2008 | Park et al. | | 2009/0177282 A1 | 7/2009 | Bureau et al. |
| 2008/0147073 A1 | 6/2008 | Ammann et al. | | 2009/0187193 A1 | 7/2009 | Maroney et al. |
| 2008/0161815 A1 | 7/2008 | Schoenefeld et al. | | 2009/0204225 A1 | 8/2009 | Meridew et al. |
| 2008/0161816 A1 | 7/2008 | Stevens et al. | | 2009/0209884 A1 | 8/2009 | Van Vorhis et al. |
| 2008/0172125 A1 | 7/2008 | Ek | | 2009/0209961 A1 | 8/2009 | Ferrante et al. |
| 2008/0195099 A1 | 8/2008 | Minas | | 2009/0210067 A1 | 8/2009 | Meridew |
| 2008/0195107 A1 | 8/2008 | Cuckler et al. | | 2009/0222014 A1 | 9/2009 | Bojarski et al. |
| 2008/0195108 A1 | 8/2008 | Bhatnagar et al. | | 2009/0222015 A1 | 9/2009 | Park et al. |
| 2008/0195109 A1 | 8/2008 | Hunter et al. | | 2009/0222016 A1 | 9/2009 | Park et al. |
| 2008/0195216 A1 | 8/2008 | Philipp | | 2009/0222103 A1 | 9/2009 | Fitz et al. |
| 2008/0200926 A1 | 8/2008 | Verard et al. | | 2009/0226068 A1 | 9/2009 | Fitz et al. |
| 2008/0208200 A1 | 8/2008 | Crofford | | 2009/0228016 A1 | 9/2009 | Alvarez et al. |
| 2008/0208353 A1 | 8/2008 | Kumar et al. | | 2009/0234360 A1 | 9/2009 | Alexander |
| 2008/0215059 A1 | 9/2008 | Carignan et al. | | 2009/0248044 A1 | 10/2009 | Amiot et al. |
| 2008/0221699 A1 | 9/2008 | Meridew et al. | | 2009/0254093 A1 | 10/2009 | White et al. |
| 2008/0230422 A1 | 9/2008 | Pleil et al. | | 2009/0254367 A1 | 10/2009 | Belcher et al. |
| 2008/0234664 A1 | 9/2008 | May et al. | | 2009/0259312 A1 | 10/2009 | Shterling et al. |
| 2008/0234683 A1 | 9/2008 | May | | 2009/0270868 A1 | 10/2009 | Park et al. |
| 2008/0234685 A1 | 9/2008 | Gjerde | | 2009/0274350 A1 | 11/2009 | Pavlovskaia et al. |
| 2008/0234833 A1 | 9/2008 | Bandoh et al. | | 2009/0287217 A1 | 11/2009 | Ammann et al. |
| 2008/0243127 A1 | 10/2008 | Lang et al. | | 2009/0306676 A1 | 12/2009 | Lang et al. |
| 2008/0255674 A1 | 10/2008 | Rahaman et al. | | 2009/0307893 A1 | 12/2009 | Burdulis, Jr. et al. |
| 2008/0257363 A1 | 10/2008 | Schoenefeld et al. | | 2009/0318836 A1 | 12/2009 | Stone et al. |
| 2008/0262500 A1 | 10/2008 | Collazo | | 2009/0318921 A1 | 12/2009 | White et al. |
| 2008/0262624 A1 | 10/2008 | White et al. | | 2010/0010493 A1 | 1/2010 | Dower |
| 2008/0269906 A1 | 10/2008 | Iannotti et al. | | 2010/0016984 A1 | 1/2010 | Trabish |
| 2008/0275452 A1 | 11/2008 | Lang et al. | | 2010/0016986 A1 | 1/2010 | Trabish |
| 2008/0281328 A1 | 11/2008 | Lang et al. | | 2010/0023015 A1 | 1/2010 | Park |
| 2008/0281329 A1 | 11/2008 | Fitz et al. | | 2010/0030231 A1 | 2/2010 | Revie et al. |
| 2008/0281426 A1 | 11/2008 | Fitz et al. | | 2010/0036404 A1 | 2/2010 | Yi et al. |
| 2008/0287954 A1 | 11/2008 | Kunz et al. | | 2010/0042105 A1 | 2/2010 | Park et al. |
| 2008/0294170 A1 | 11/2008 | O'Brien | | 2010/0049195 A1 | 2/2010 | Park et al. |
| 2008/0294266 A1 | 11/2008 | Steinberg | | 2010/0049327 A1 | 2/2010 | Isch et al. |
| 2008/0300600 A1 | 12/2008 | Guelat et al. | | 2010/0057088 A1 | 3/2010 | Shah |
| 2008/0306485 A1 | 12/2008 | Coon et al. | | 2010/0076439 A1 | 3/2010 | Hatch |
| 2008/0306558 A1 | 12/2008 | Hakki | | 2010/0076505 A1 | 3/2010 | Borja |
| 2008/0312659 A1 | 12/2008 | Metzger et al. | | 2010/0076563 A1 | 3/2010 | Otto et al. |
| 2008/0319448 A1 | 12/2008 | Lavallee et al. | | 2010/0076571 A1 | 3/2010 | Hatch |
| 2009/0012526 A1 | 1/2009 | Fletcher | | 2010/0082034 A1 | 4/2010 | Remia |
| 2009/0018546 A1 | 1/2009 | Daley | | 2010/0082035 A1 | 4/2010 | Keefer |
| 2009/0018666 A1 | 1/2009 | Grundei et al. | | 2010/0087829 A1 | 4/2010 | Metzger et al. |
| 2009/0024131 A1 | 1/2009 | Metzger et al. | | 2010/0094295 A1 | 4/2010 | Schnieders et al. |
| 2009/0043556 A1 | 2/2009 | Axelson et al. | | 2010/0105011 A1 | 4/2010 | Karkar et al. |
| 2009/0076371 A1 | 3/2009 | Lang et al. | | 2010/0121334 A1 | 5/2010 | Couture et al. |
| 2009/0076512 A1 | 3/2009 | Ammann et al. | | 2010/0121335 A1 | 5/2010 | Penenberg et al. |
| 2009/0076520 A1 | 3/2009 | Choi | | 2010/0131073 A1 | 5/2010 | Meridew et al. |
| 2009/0082770 A1 | 3/2009 | Worner et al. | | 2010/0136214 A1 | 6/2010 | Kumar |
| 2009/0082774 A1 | 3/2009 | Oti et al. | | 2010/0137869 A1 | 6/2010 | Borja et al. |
| 2009/0087276 A1 | 4/2009 | Rose | | 2010/0137924 A1 | 6/2010 | Tuke et al. |
| 2009/0088674 A1 | 4/2009 | Caillouette et al. | | 2010/0145343 A1 | 6/2010 | Johnson et al. |
| 2009/0088753 A1 | 4/2009 | Aram et al. | | 2010/0145344 A1 | 6/2010 | Jordan et al. |
| 2009/0088754 A1 | 4/2009 | Aker et al. | | 2010/0145466 A1 | 6/2010 | Slone |
| 2009/0088755 A1 | 4/2009 | Aker et al. | | 2010/0152782 A1 | 6/2010 | Stone et al. |
| 2009/0088758 A1 | 4/2009 | Bennett | | 2010/0160917 A1 | 6/2010 | Fitz et al. |

| | | | | | | |
|---|---|---|---|---|---|---|
| 2010/0168752 A1 | 7/2010 | Edwards | | 2012/0109138 A1 | 5/2012 | Meridew et al. |
| 2010/0168754 A1 | 7/2010 | Fitz et al. | | 2012/0109226 A1 | 5/2012 | Iannotti et al. |
| 2010/0168857 A1 | 7/2010 | Hatch | | 2012/0130382 A1 | 5/2012 | Iannotti et al. |
| 2010/0179663 A1 | 7/2010 | Steinberg | | 2012/0136365 A1 | 5/2012 | Iannotti et al. |
| 2010/0185202 A1 | 7/2010 | Lester et al. | | 2012/0141034 A1 | 6/2012 | Iannotti et al. |
| 2010/0191244 A1 | 7/2010 | White et al. | | 2012/0143197 A1 | 6/2012 | Lang et al. |
| 2010/0198224 A1 | 8/2010 | Metzger et al. | | 2012/0143267 A1 | 6/2012 | Iannotti et al. |
| 2010/0212138 A1 | 8/2010 | Carroll et al. | | 2012/0209276 A1 | 8/2012 | Schuster |
| 2010/0217109 A1 | 8/2010 | Belcher | | 2012/0215225 A1 | 8/2012 | Philippon et al. |
| 2010/0217270 A1 | 8/2010 | Polinski et al. | | 2012/0221017 A1 | 8/2012 | Bonutti |
| 2010/0217336 A1 | 8/2010 | Crawford et al. | | 2012/0226283 A1 | 9/2012 | Meridew et al. |
| 2010/0217338 A1 | 8/2010 | Carroll et al. | | 2012/0232596 A1 | 9/2012 | Ribeiro |
| 2010/0228257 A1 | 9/2010 | Bonutti | | 2012/0259335 A1 | 10/2012 | Scifert et al. |
| 2010/0249657 A1 | 9/2010 | Nycz et al. | | 2012/0265208 A1 | 10/2012 | Smith |
| 2010/0249796 A1 | 9/2010 | Nycz | | 2012/0271314 A1 | 10/2012 | Stemniski et al. |
| 2010/0262150 A1 | 10/2010 | Lian | | 2012/0271366 A1 | 10/2012 | Katrana et al. |
| 2010/0274253 A1 | 10/2010 | Ure | | 2012/0276509 A1 | 11/2012 | Iannotti et al. |
| 2010/0281678 A1 | 11/2010 | Burdulis, Jr. et al. | | 2012/0277751 A1 | 11/2012 | Catanzarite et al. |
| 2010/0286700 A1 | 11/2010 | Snider et al. | | 2012/0289965 A1 | 11/2012 | Gelaude et al. |
| 2010/0286789 A1 | 11/2010 | Meridew | | 2012/0296339 A1 | 11/2012 | Iannotti et al. |
| 2010/0292743 A1 | 11/2010 | Singhal et al. | | 2012/0303004 A1 | 11/2012 | Uthgenannt et al. |
| 2010/0305574 A1 | 12/2010 | Fitz et al. | | 2012/0303033 A1 | 11/2012 | Weiner et al. |
| 2010/0318088 A1 | 12/2010 | Warne et al. | | 2012/0310399 A1 | 12/2012 | Metzger |
| 2010/0324692 A1 | 12/2010 | Uthgenannt et al. | | 2012/0316564 A1 | 12/2012 | Serbousek et al. |
| 2011/0004317 A1 | 1/2011 | Hacking et al. | | 2012/0323246 A1 | 12/2012 | Catanzarite et al. |
| 2011/0009869 A1 | 1/2011 | Marino et al. | | 2013/0001121 A1 | 1/2013 | Metzger |
| 2011/0015636 A1 | 1/2011 | Katrana et al. | | 2013/0006250 A1 | 1/2013 | Metzger et al. |
| 2011/0015639 A1 | 1/2011 | Metzger et al. | | 2013/0035766 A1 | 2/2013 | Meridew |
| 2011/0015752 A1 | 1/2011 | Meridew | | 2013/0119579 A1 | 5/2013 | Iannotti et al. |
| 2011/0015753 A1 | 1/2011 | Meridew | | | | |
| 2011/0022049 A1 | 1/2011 | Huebner et al. | | | | |
| 2011/0029091 A1 | 2/2011 | Bojarski et al. | | FOREIGN PATENT DOCUMENTS | | |
| 2011/0029093 A1 | 2/2011 | Bojarski et al. | | | | |
| 2011/0029116 A1 | 2/2011 | Jordan et al. | | CA | 2505371 A1 | 5/2004 |
| 2011/0035012 A1 | 2/2011 | Linares | | CA | 2505419 A1 | 6/2004 |
| 2011/0040303 A1 | 2/2011 | Iannotti | | CA | 2506849 A1 | 6/2004 |
| 2011/0040334 A1 | 2/2011 | Kaes et al. | | CA | 2546958 A1 | 6/2005 |
| 2011/0046735 A1 | 2/2011 | Metzger et al. | | CA | 2546965 A1 | 6/2005 |
| 2011/0054478 A1 | 3/2011 | Vanasse et al. | | CA | 2588907 A1 | 6/2006 |
| 2011/0066193 A1 | 3/2011 | Lang et al. | | CA | 2590534 A1 | 6/2006 |
| 2011/0066245 A1 | 3/2011 | Lang et al. | | CN | 1630495 A | 6/2005 |
| 2011/0071528 A1 | 3/2011 | Carson | | CN | 1728976 A | 2/2006 |
| 2011/0071529 A1 | 3/2011 | Carson | | CN | 1729483 A | 2/2006 |
| 2011/0071530 A1 | 3/2011 | Carson | | CN | 1729484 A | 2/2006 |
| 2011/0071532 A1 | 3/2011 | Carson | | CN | 1913844 A | 2/2007 |
| 2011/0071533 A1 | 3/2011 | Metzger et al. | | CN | 101111197 A | 1/2008 |
| 2011/0092804 A1 | 4/2011 | Schoenefeld et al. | | DE | 3447365 A1 | 7/1986 |
| 2011/0093086 A1 | 4/2011 | Witt et al. | | DE | 04219939 A1 | 12/1993 |
| 2011/0106254 A1 | 5/2011 | Abel et al. | | DE | 4421153 A1 | 12/1995 |
| 2011/0125264 A1 | 5/2011 | Bagga et al. | | DE | 102009028503 A1 | 2/2011 |
| 2011/0130795 A1 | 6/2011 | Ball | | DE | 102011082902 A1 | 3/2012 |
| 2011/0151027 A1 | 6/2011 | Clineff et al. | | DE | 102012205820 A1 | 10/2012 |
| 2011/0151259 A1 | 6/2011 | Jarman-Smith et al. | | DE | 112010003901 T5 | 11/2012 |
| 2011/0153025 A1 | 6/2011 | McMinn | | EP | 0114505 A1 | 8/1984 |
| 2011/0160736 A1 | 6/2011 | Meridew et al. | | EP | 0326768 A2 | 8/1989 |
| 2011/0160867 A1 | 6/2011 | Meridew et al. | | EP | 0579868 A2 | 1/1994 |
| 2011/0166578 A1 | 7/2011 | Stone et al. | | EP | 0591985 A1 | 4/1994 |
| 2011/0172672 A1 | 7/2011 | Dubeau et al. | | EP | 0645984 A1 | 4/1995 |
| 2011/0184419 A1 | 7/2011 | Meridew et al. | | EP | 0650706 A1 | 5/1995 |
| 2011/0184424 A1 | 7/2011 | Isch et al. | | EP | 0916324 A2 | 5/1999 |
| 2011/0184526 A1 | 7/2011 | White et al. | | EP | 1321107 A1 | 6/2003 |
| 2011/0190899 A1 | 8/2011 | Pierce et al. | | EP | 1327424 A1 | 7/2003 |
| 2011/0190901 A1 | 8/2011 | Weissberg et al. | | EP | 1437102 A1 | 7/2004 |
| 2011/0213376 A1 | 9/2011 | Maxson et al. | | EP | 01486900 A1 | 12/2004 |
| 2011/0214279 A1 | 9/2011 | Park et al. | | EP | 1634551 A2 | 3/2006 |
| 2011/0218545 A1 | 9/2011 | Catanzarite et al. | | EP | 1852072 A2 | 7/2007 |
| 2011/0251617 A1 | 10/2011 | Ammann et al. | | EP | 1832239 A1 | 9/2007 |
| 2011/0257657 A1 | 10/2011 | Turner et al. | | EP | 2029061 A2 | 3/2009 |
| 2011/0269100 A1 | 11/2011 | Furrer et al. | | EP | 2168507 A2 | 3/2010 |
| 2011/0275032 A1 | 11/2011 | Tardieu et al. | | EP | 2303146 A1 | 4/2011 |
| 2011/0295887 A1 | 12/2011 | Palmese et al. | | EP | 2303192 A1 | 4/2011 |
| 2012/0010619 A1 | 1/2012 | Barsoum | | EP | 2352445 A1 | 8/2011 |
| 2012/0010710 A1 | 1/2012 | Frigg | | EP | 2396741 A1 | 12/2011 |
| 2012/0010711 A1 | 1/2012 | Antonyshyn et al. | | EP | 2398381 A1 | 12/2011 |
| 2012/0065640 A1 | 3/2012 | Metzger et al. | | EP | 2403437 A2 | 1/2012 |
| 2012/0078259 A1 | 3/2012 | Meridew | | EP | 2491873 A2 | 8/2012 |
| 2012/0089595 A1 | 4/2012 | Jaecksch | | FR | 2659226 A1 | 9/1991 |
| 2012/0101586 A1 | 4/2012 | Carson | | FR | 2721195 A1 | 12/1995 |
| 2012/0109137 A1 | 5/2012 | Iannotti et al. | | FR | 2768916 A1 | 4/1999 |
| | | | | GB | 2094590 A | 9/1982 |

| | | | |
|---|---|---|---|
| GB | 2197790 A | 6/1988 | |
| GB | 2442441 A | 4/2008 | |
| GB | 2447702 A | 9/2008 | |
| GB | 2483980 A | 3/2012 | |
| GB | 2486390 A | 6/2012 | |
| GB | 2490220 A | 10/2012 | |
| GB | 2491526 A | 12/2012 | |
| JP | 59157715 A | 9/1984 | |
| JP | 60231208 A | 11/1985 | |
| JP | 2011505080 A | 2/2011 | |
| JP | 2011527885 A | 11/2011 | |
| KR | 20050072500 A | 7/2005 | |
| KR | 20050084024 A | 8/2005 | |
| RU | 2083179 C1 | 7/1997 | |
| RU | 2113182 C1 | 6/1998 | |
| RU | 2125835 C1 | 2/1999 | |
| RU | 2138223 C1 | 9/1999 | |
| RU | 2175534 C2 | 11/2001 | |
| RU | 2187975 C1 | 8/2002 | |
| TW | 231755 | 5/2005 | |
| WO | WO-8807840 A1 | 10/1988 | |
| WO | WO-9107139 A1 | 5/1991 | |
| WO | WO-9325157 A1 | 12/1993 | |
| WO | WO-9528688 A1 | 10/1995 | |
| WO | WO-9952473 A1 | 10/1999 | |
| WO | WO-9959106 A1 | 11/1999 | |
| WO | WO-0170142 A1 | 9/2001 | |
| WO | WO-0184479 A1 | 11/2001 | |
| WO | WO-0217821 A2 | 3/2002 | |
| WO | WO-0226145 | 4/2002 | |
| WO | WO-0236024 A1 | 5/2002 | |
| WO | WO-02096268 A2 | 12/2002 | |
| WO | WO-03051210 A2 | 6/2003 | |
| WO | WO-03051211 A1 | 6/2003 | |
| WO | WO-2004032806 A1 | 4/2004 | |
| WO | WO-2004049981 A2 | 6/2004 | |
| WO | WO-2004051301 A2 | 6/2004 | |
| WO | WO-200407806 A2 | 9/2004 | |
| WO | WO-2005005124 A1 | 6/2005 | |
| WO | WO-2005051239 A1 | 6/2005 | |
| WO | WO-2005077039 A2 | 8/2005 | |
| WO | WO-2006058057 A2 | 6/2006 | |
| WO | WO-2006060795 A1 | 6/2006 | |
| WO | WO-2006092600 A1 | 9/2006 | |
| WO | WO-2006127486 A2 | 11/2006 | |
| WO | WO-2006134345 A1 | 12/2006 | |
| WO | WO-2006136955 A1 | 12/2006 | |
| WO | WO-2007041375 A2 | 4/2007 | |
| WO | WO-2007053572 A2 | 5/2007 | |
| WO | WO-2007062079 A2 | 5/2007 | |
| WO | WO-2007092841 A2 | 8/2007 | |
| WO | WO-2007137327 A1 | 12/2007 | |
| WO | WO-2007145937 A2 | 12/2007 | |
| WO | WO-2008014618 A1 | 2/2008 | |
| WO | WO-2008021494 A2 | 2/2008 | |
| WO | WO-2008040961 A1 | 4/2008 | |
| WO | WO-2008044055 A1 | 4/2008 | |
| WO | WO-2008091358 A1 | 7/2008 | |
| WO | WO-2008101090 A2 | 8/2008 | |
| WO | WO-2008109751 A1 | 9/2008 | |
| WO | WO-2008112996 A1 | 9/2008 | |
| WO | WO-200814074 A1 | 11/2008 | |
| WO | WO-2009001083 A1 | 12/2008 | |
| WO | WO-2009025783 A1 | 2/2009 | |
| WO | WO-2009073781 A2 | 6/2009 | |
| WO | WO-2009129063 A1 | 10/2009 | |
| WO | WO-2009129067 A2 | 10/2009 | |
| WO | WO-2010033431 A1 | 3/2010 | |
| WO | WO-2010093902 A1 | 8/2010 | |
| WO | WO-2010096553 A1 | 8/2010 | |
| WO | WO-2010096557 A2 | 8/2010 | |
| WO | WO-2010124164 A1 | 10/2010 | |
| WO | WO-2010144705 A1 | 12/2010 | |
| WO | WO-2010148103 A1 | 12/2010 | |
| WO | WO-2011018458 A1 | 2/2011 | |
| WO | WO-2011041398 A1 | 4/2011 | |
| WO | WO-2011060536 A1 | 5/2011 | |
| WO | WO-2011019797 A3 | 7/2011 | |
| WO | WO-2011106711 A1 | 9/2011 | |
| WO | WO-2011109260 A1 | 9/2011 | |
| WO | WO-2011110374 A1 | 9/2011 | |
| WO | WO-2012006444 A2 | 1/2012 | |
| WO | WO-2012033821 A1 | 3/2012 | |
| WO | WO-2012058344 A1 | 5/2012 | |
| WO | WO-2012061042 A1 | 5/2012 | |
| WO | WO-2012058353 A4 | 6/2012 | |
| WO | WO-2012058355 A4 | 7/2012 | |
| WO | WO-2012058349 A4 | 8/2012 | |
| WO | WO-2012116206 A1 | 8/2012 | |
| WO | WO-2012158917 A1 | 11/2012 | |
| WO | WO-2012173929 A1 | 12/2012 | |
| WO | WO-2012174008 A1 | 12/2012 | |

OTHER PUBLICATIONS

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Charl P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazen, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty," The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Biomet "Oxford® Partial Knee" brochure, 8 pages (Feb. 2011).

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionsverfahrens," Zuma Thema: Computergestützte orthopädische Chirugie, Der Orthopäde 29:641-644 Springer-Verlag (Jul. 2000) Translation provided: Thoma, W. "Endoprosthetic care of the knee joint based on a 3D computer chromatography subtraction process," Topic: Computer-aided orthopedic surgery. Orthopedist 2000 29:641-644 Springer Verlag (Jul. 2000).

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

"Comprehensive® Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

Friedman, R.J. et al., "The Use of Computerized Tomography in the Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478, filed Aug. 29, 2011.

International Search Report and Written Opinion mailed Feb. 6, 2013 for PCT/US2012/060842, which claims benefit of U.S. Appl. No. 13/653,868, filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

"Max-Ti™ Modular Protrusio Cage," Surgical Technique brochure. Biomet Orthopedics, Inc. (2003) 10 sheets.

"Max-Ti™ Modular Protrusio Cage," Surgical Technique brochure. Biomet Orthopedics, Inc. (2006) 12 sheets.

"Par 5™ Protrusio Acetabular Reconstruction System," brochure. (2006) Biomet Orthopedics, Inc. 12 sheets.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability mailed Sep. 6, 2013 for PCT/US2012/026356 claiming benefit of U.S. Appl. No. 13/041,883, filed Mar. 7, 2011.

International Search Report and Written Opinion mailed Oct. 14, 2013 for PCT/US2013/057097 claiming benefit of U.S. Appl. No. 13/597,478, filed Aug. 29, 2012.

* cited by examiner

PATIENT-SPECIFIC ACETABULAR ALIGNMENT GUIDES

CROSS-REFERENCE TO RELATED APPLICATIONS

This application claims the benefit of U.S. Provisional Application No. 61/446,660, filed on Feb. 25, 2011.

This application is a continuation-in-part of U.S. application Ser. Nos. 13/041,469, 13/041,495, 13/041,665 and 13/041,883, each filed on Mar. 7, 2011, each of which is a continuation-in-part of U.S. application Ser. No. 12/978,069 filed Dec. 23, 2010, which is a continuation-in-part of U.S. application Ser. No. 12/973,214, filed Dec. 20, 2010, which is a continuation-in-part of U.S. application Ser. No. 12/955,361 filed Nov. 29, 2010, which is a continuation-in-part of U.S. application Ser. Nos. 12/938,913 and 12/938,905, both filed Nov. 3, 2010, each of which is a continuation-in-part of U.S. application Ser. No. 12/893,306, filed Sep. 29, 2010, which is a continuation-in-part of U.S. application Ser. No. 12/888,005, filed Sep. 22, 2010, which is a continuation-in-part of U.S. application Ser. No. 12/714,023, filed Feb. 26, 2010, which is a continuation-in-part of U.S. application Ser. No. 12/571,969, filed Oct. 1, 2009, which is a continuation-in-part of U.S. application Ser. No. 12/486,992, filed Jun. 18, 2009, and is a continuation-in-part of U.S. application Ser. No. 12/389,901, filed Feb. 20, 2009, which is a continuation-in-part of U.S. application Ser. No. 12/211,407, filed Sep. 16, 2008, which is a continuation-in-part of U.S. application Ser. No. 12/039,849, filed Feb. 29, 2008, which: (1) claims the benefit of U.S. Provisional Application No. 60/953,620, filed on Aug. 2, 2007, U.S. Provisional Application No. 60/947,813, filed on Jul. 3, 2007, U.S. Provisional Application No. 60/911,297, filed on Apr. 12, 2007, and U.S. Provisional Application No. 60/892,349, filed on Mar. 1, 2007; (2) is a continuation-in-part U.S. application Ser. No. 11/756,057, filed on May 31, 2007, which claims the benefit of U.S. Provisional Application No. 60/812,694, filed on Jun. 9, 2006; (3) is a continuation-in-part of U.S. application Ser. No. 11/971,390, filed on Jan. 9, 2008, which is a continuation-in-part of U.S. application Ser. No. 11/363,548, filed on Feb. 27, 2006, now U.S. Pat. No. 7,780,672, issued on Aug. 24, 2010; and (4) is a continuation-in-part of U.S. application Ser. No. 12/025,414, filed on Feb. 4, 2008, which claims the benefit of U.S. Provisional Application No. 60/953,637, filed on Aug. 2, 2007.

This application is continuation-in-part of U.S. application Ser. No. 12/872,663, filed on Aug. 31, 2010, which claims the benefit of U.S. Provisional Application No. 61/310,752 filed on Mar. 5, 2010.

This application is a continuation-in-part of U.S. application Ser. No. 12/483,807, filed on Jun. 12, 2009, which is a continuation-in-part of U.S. application Ser. No. 12/371,096, filed on Feb. 13, 2009, which is a continuation-in-part of U.S. application Ser. No. 12/103,824, filed on Apr. 16, 2008, which claims the benefit of U.S. Provisional Application No. 60/912,178, filed on Apr. 17, 2007.

This application is also a continuation-in-part of U.S. application Ser. No. 12/103,834, filed on Apr. 16, 2008, which claims the benefit of U.S. Provisional Application No. 60/912,178, filed on Apr. 17, 2007.

The disclosures of the above applications are incorporated herein by reference.

INTRODUCTION

The present teachings provide a patient-specific acetabular alignment guide and related instruments for guiding an acetabular implant into the acetabulum of a patient.

SUMMARY

The present teachings provide an acetabular device. In one aspect, the acetabular system includes a patient-specific acetabular alignment guide including a bone engagement surface. The bone engagement surface has a first portion configured and shaped to be conforming and complementary to an acetabular rim surface and a second portion configured and shaped to be conforming and complementary to a periacetabular area of an acetabulum of a patient. The acetabular alignment guide includes a plurality of guiding formations extending through the second portion for guiding a plurality of alignment pins therethrough. The bone engagement surface and the plurality of guiding formations are prepared from a three-dimensional model of the acetabulum of the specific patient reconstructed pre-operatively from a scan of the patient.

The acetabular device can also include an acetabular inserter including a handle, a shaft and an acetabular coupler and a first alignment adapter removably coupled to the shaft of the acetabular inserter. The first alignment adapter includes a plurality of apertures configured to correspond to the guiding formations of the acetabular alignment guide, such that the alignment pins can pass through the apertures of the alignment adapter after the acetabular alignment guide is removed without removing the alignment pins from the patient.

The present teachings also provide a method for inserting an acetabular implant into the acetabulum of a patient. The method includes engaging a patient-specific surface of the acetabular alignment guide to a complementary rim surface and periacetabular area of a patient and inserting a plurality of alignment pins through corresponding alignment apertures of the acetabular alignment guide and into the periacetabular area of the patient. The method further includes removing the acetabular alignment guide without removing the alignment pins from the patient, guiding a first alignment adapter coupled to an acetabular inserter over the alignment pins, and implanting the acetabular implant with the acetabular inserter.

The present teachings provide an acetabular device that includes an annular acetabular guide including a first surface and a second surface opposite to the first surface. The first surface is patient-specific and made to conform to an acetabular rim surface around an acetabulum of a patient in accordance with a three-dimensional image of the acetabulum of the patient. The acetabular guide includes a cylindrical inner guiding surface oriented at patient-specific anteversion and abduction angles relative to the first surface. The acetabular device also includes a patient-specific adapter having an outer surface mateable with the inner surface of the acetabular guide and having a quick-connection component for coupling to a non-custom acetabular instrument.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

Figure 1:
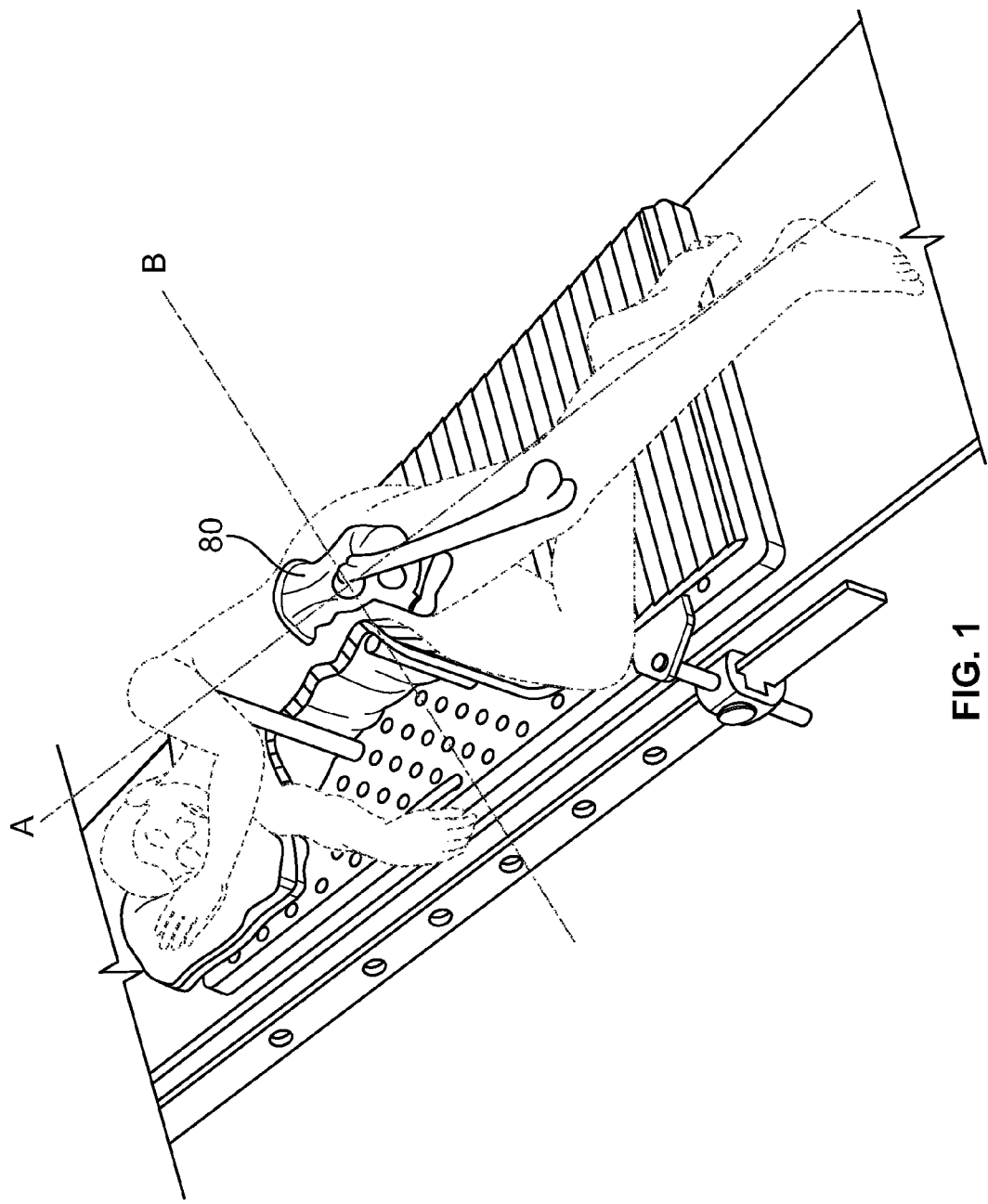
FIG. 1 is an exemplary illustration of a patient in preparation of an acetabular implant procedure.

The following description is merely exemplary in nature and is in no way intended to limit the present teachings, applications, or uses.

The present teachings generally provide a patient-specific acetabular guide and associated inserter for use in orthopedic surgery, such as in joint replacement or revision surgery, for example. The patient-specific alignment guides can be used either with conventional or patient-specific implant components prepared with computer-assisted image methods. Computer modeling for obtaining three dimensional images of the patient's anatomy using MRI or CT scans of the patient's anatomy, the patient-specific prosthesis components, and the patient-specific guides and templates can be provided by various CAD programs and/or software available, for example, by Materialise USA, Ann Arbor, Mich.

Patient-specific alignment guides and implants are generally configured to match the anatomy of a specific patient. The patient-specific alignment guides are generally formed using computer modeling based on the patient's 3-D anatomic image and have an engagement surface that is made to conformingly contact and match a three-dimensional image/model of the patient's bone surface (with or without cartilage or other soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan. The patient-specific alignment guides can be used in minimally invasive surgery, and in particular in surgery with multiple minimally-invasive incisions. Various alignment guides and pre-operative planning procedures are disclosed in commonly assigned and co-pending U.S. patent application Ser. No. 11/756,057, filed on May 31, 2007; U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; and U.S. patent application Ser. No. 12/025,414, filed Feb. 4, 2008. The disclosures of the above applications are incorporated herein by reference.

As disclosed, for example, in above-referenced U.S. patent application Ser. No. 11/756,057, filed on May 31, 2007; in the pre-operative planning stage for a joint replacement or revision procedure, an MRI scan or a series of CT scans of the relevant anatomy of the patient, such as, for example, the entire leg of the joint to be reconstructed, can be performed at a medical facility or doctor's office. The scan data obtained can be sent to a manufacturer. The scan data can be used to construct a three-dimensional image/model of the joint and provide an initial implant fitting and alignment in a computer file form or other computer representation. The initial implant fitting and alignment can be obtained using an alignment method, such as alignment protocols used by individual surgeons.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review. The surgeon can incrementally manipulate the position of images of implant components in an interactive image of the joint. Additionally, the surgeon can select or modify resection planes, types of implants and orientations of implant insertion. For example, the surgeon may select patient-specific anteversion and abduction angles for acetabular implants, as discussed below. After the surgeon modifies and/or approves the surgical plan, the surgeon can send the final, approved plan to the manufacturer.

After the surgical plan is approved by the surgeon, patient-specific alignment guides can be developed using a CAD program or other imaging software, such as the software provided by Materialise, for example, according to the surgical plan. Computer instructions of tool paths for machining the patient-specific alignment guides can be generated and stored in a tool path data file. The tool path can be provided as input to a CNC mill or other automated machining system, and the alignment guides can be machined from polymer, ceramic, metal or other suitable material, and sterilized. The sterilized alignment guides can be shipped to the surgeon or medical facility, for use during the surgical procedure.

The present teachings provide a patient-specific acetabular guide and associated inserter for inserting an acetabular implant in the acetabulum of a patient's pelvis in a guided orientation at least about first and second non-parallel anatomic axes. Referring to FIGS. 1, 3A and 3B, the first anatomic axis indicated at "A", passes through the acetabulum 82 of a patient's pelvis 80 (only half of the pelvis is shown) and is oriented generally in a superior/inferior direction relative to the patient. The second anatomic axis is indicated at "B" and is substantially perpendicular to the first axis A. As described below, the present teachings provide instruments and methods for guiding, orienting and positioning an acetabular implant 200 at a selected angle of anteversion relative to the axis A, as shown in FIG. 3A, and at a selected angle of abduction relative to the axis B, as also shown in FIG. 3B. The anteversion and abduction angles can be determined interactive or other surgeon input and can be patient-specific.

Figure 1A:
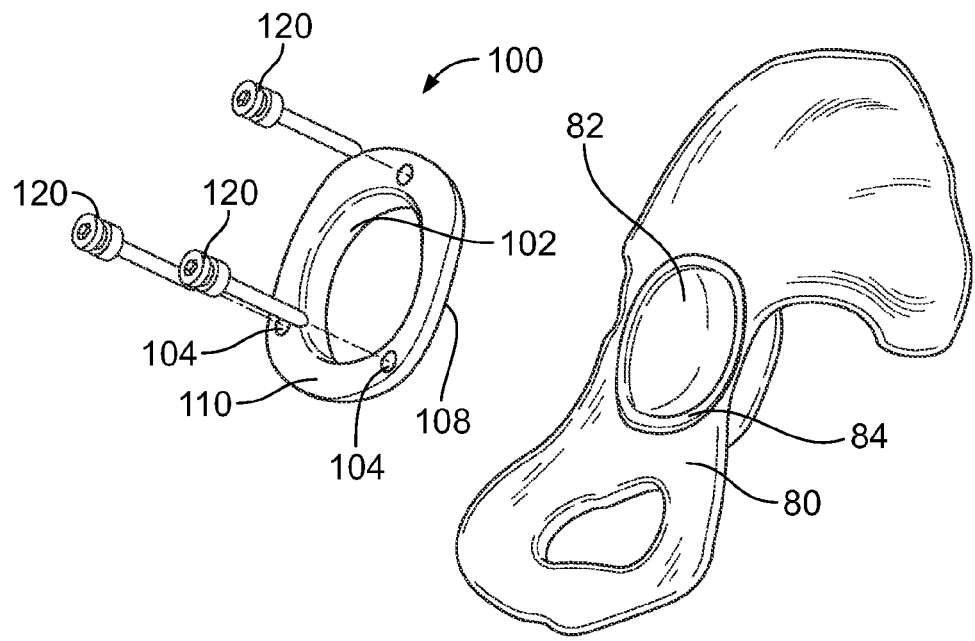
FIG. 1A is a perspective view of an acetabular guide according to the present teachings, the acetabular guide shown in relation to a patient's anatomy.

Referring to FIG. 1A, an exemplary acetabular guide 100 according to the present teachings can include a first surface 108 for engaging an area surrounding the acetabulum 82 and a second surface 110 opposite to the first surface 108. The acetabulum-engaging first surface 108 can be custom-made or patient-specific to conform and mirror an acetabular rim surface 84 around the acetabulum 82 of a specific patient by using three-dimensional image or model of the acetabulum and surrounding pelvic area of the patient, as described above. The first surface 108 enables the acetabular guide to nest or closely mate relative to the acetabulum 82 of the patient.

Figure 2:
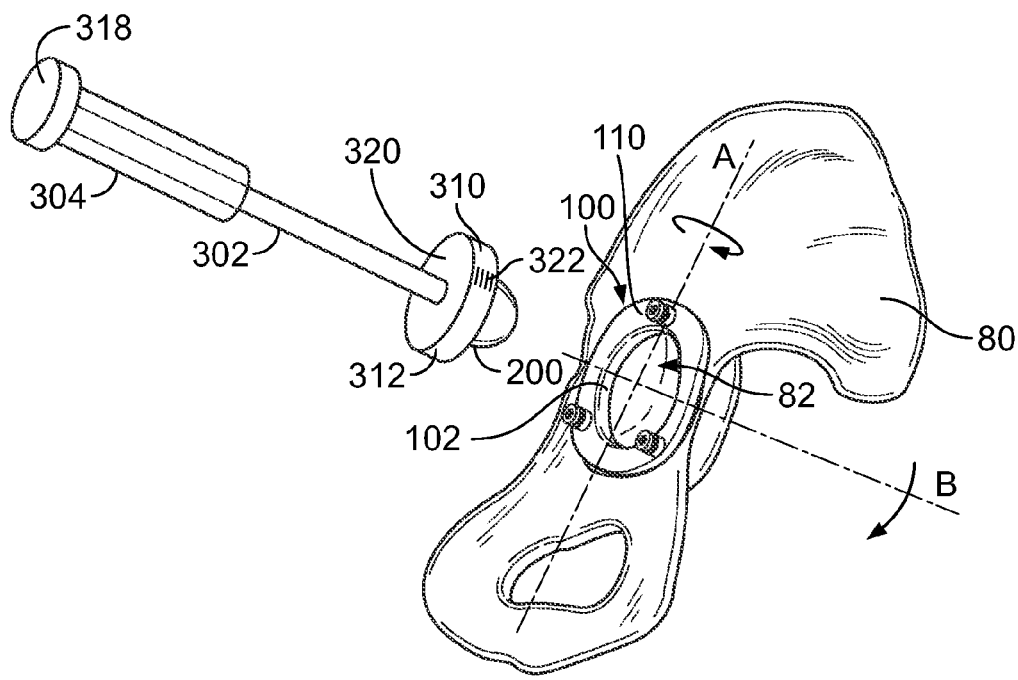
FIG. 2 is an environmental perspective view of the acetabular guide of FIG. 1A shown with an acetabular inserter holding an acetabular implant according to the present teachings.

The acetabular guide 100 can be temporarily and removably attached to the pelvis 80 using temporary fasteners 120, such as bone nails or tacks, for example, passing through corresponding holes 104 through the acetabular guide 100. The acetabular guide 100 can be annular with an opening defined by an inner surface 102. The inner surface 102 can be, for example, a cylindrical surface. The inner surface 102 can be oriented relative to the first and second surfaces 108, 110 of the acetabular guide 100 to provide a selected anteversion angle about the first axis A and a selected abduction angle relative to the axis B, as shown in FIGS. 2, 3A and 3B. The anteversion and abduction angles can be surgeon-selected and patient-specific and can be determined with surgeon input during the pre-operative planning for the specific patient. Anteversion angles can be, for example, in the range of about 10-20 degrees forward relative to the first axis A, and adduction angles can be in the range of about 40-50 degrees downward relative to the second axis B.

Figure 3:
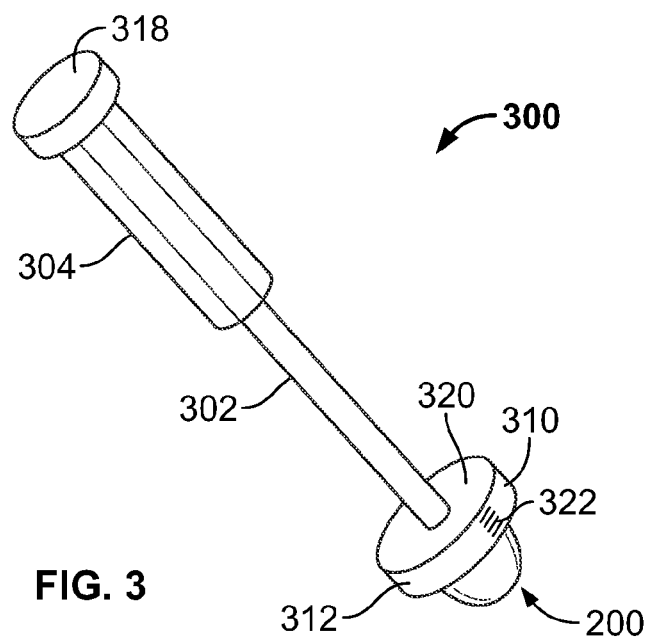
FIG. 3 is a perspective view of the acetabular inserter and acetabular implant of FIG. 2.
Figure 3A:
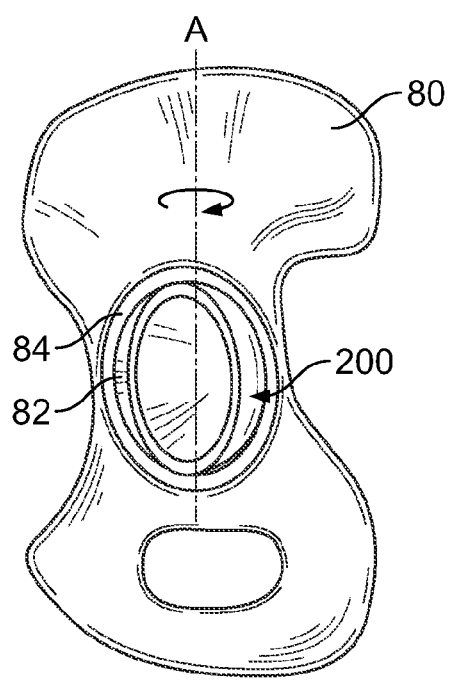
FIG. 3A is a perspective environmental view of an acetabular implant illustrating rotation about an anatomic axis A during insertion according to the present teachings.
Figure 3B:
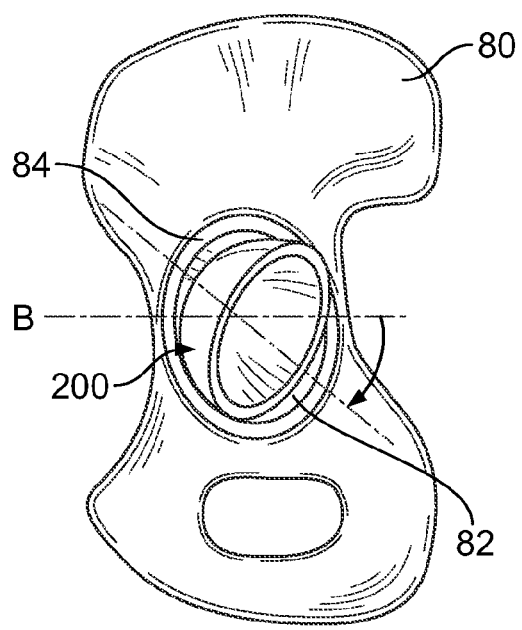
FIG. 3B is a perspective environmental view of an acetabular implant illustrating rotation about an anatomic axis B during insertion according to the present teachings.
Figure 4:
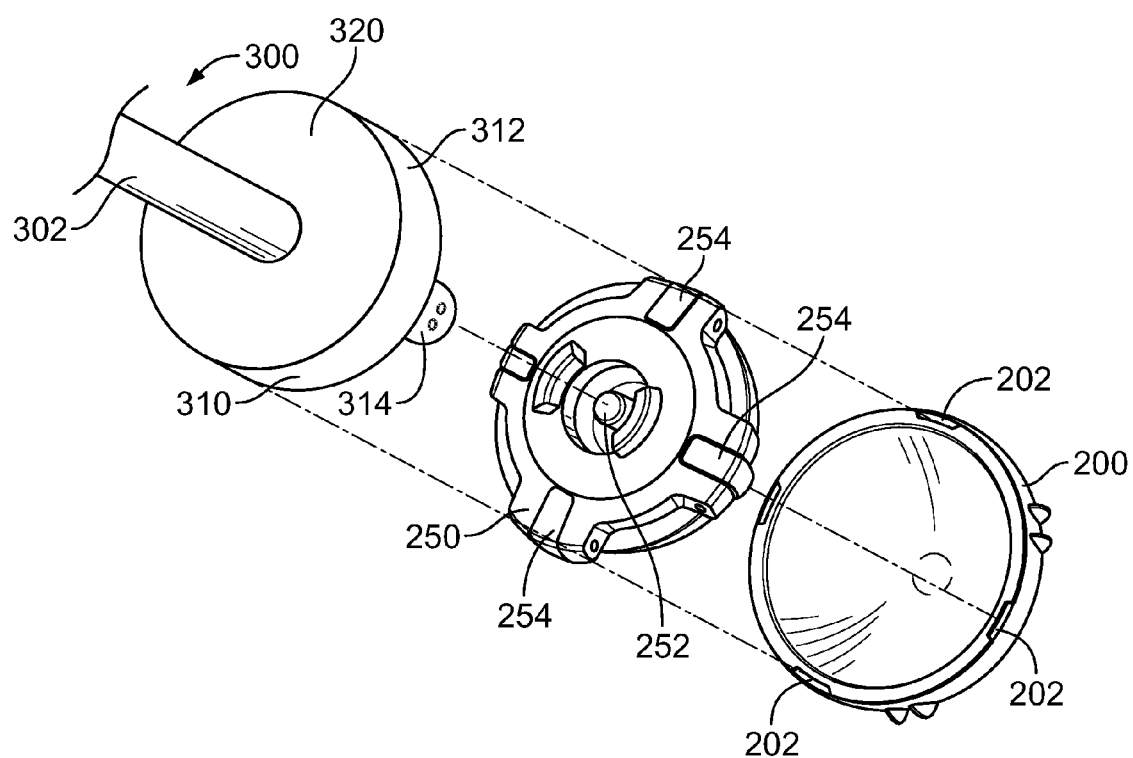
FIG. 4 is an exploded view of the acetabular inserter and acetabular implant of FIG. 3.

Referring to FIGS. 2-4, the acetabular guide 100 can be attached to the pelvis 80 around the acetabulum 72 after the acetabulum 82 has been reamed and prepared for receiving the acetabular implant 200, such as the Magnum™ acetabular cup commercially available from Biomet, Inc., Warsaw, Ind. The acetabular implant 200 can be inserted into the prepared acetabulum 82 using an inserter 300 according to the present teachings. The inserter 300, which can also function as an impactor, can include a handle 304 with a proximal impaction surface 318, a shaft 302 and a guide-engaging portion 310 having a surface with a flat or planar portion 320. The guide-engaging portion 310 can have an outer surface 312, which conforms to and is mateable with the inner surface 102 of the acetabular guide 100 for guiding the acetabular implant 200. The inner surface 102 and the outer surface 312 can be cylindrical.

Referring to FIG. 4, the inserter 300 can engage the acetabular implant 200 via an intermediate member 250, such as the intermediate member of the Magnum™ system, which is commercially available from Biomet, Inc., Warsaw, Ind. More specifically, the inserter 300 can include a distal portion 314, such as a ball-bearing bushing, which can be inserted and engage a receptacle 252 of the intermediate member 250. The acetabular implant 200 can be mounted on the inserter 300 by aligning a plurality of fingers 254 of the intermediate member 250 with corresponding cut-outs 202 on a peripheral edge of the acetabular implant 200. The acetabular implant 200 can be secured to the inserter 300 by rotating the acetabular implant 200 relative to the insert 300 until a hand-tight fit is obtained.

Referring to FIG. 2, the inserter 300 with the acetabular implant 200 mounted thereon can be directed toward the acetabular guide 100. The outer surface 312 of the guide engaging portion 310 of the inserter 300 can be brought into contact with the inner surface 102 of the acetabular guide 100, guiding the acetabular implant 200 toward the selected anteversion and abduction orientation through the acetabular guide 100. The outer surface 312 of the guide engaging portion 310 can also provide an impaction-depth feedback by alignment with the inner surface 102 of the acetabular guide. Full impaction of the acetabular implant 200 into the acetabulum 82 can be indicated when planar portion 320 and/or outer surface 312 of the guide-engaging portion 310 of the inserter 300 are flush with and do not protrude over and above the second surface 110 of the acetabular guide 100. Depth indicia 322 can also be provided on the inserter shaft 302 or on the guide-engaging portion 310 of the inserter 300, as shown in FIG. 2.

After the acetabular implant 200 is fully seated in the acetabulum 82 in the selected anteversion and abduction orientations, the inserter 300 and intermediate member 250 can be removed. The temporary fasteners 120 can be removed and the acetabular guide released.

The acetabular guide 100 can be made of any biocompatible material, such as metal, ceramic or polymer. The acetabular guide 100 can be constructed by various manufacturing methods depending of the selected material, including, for example, machining, casting, molding, stereolithography or other layer deposition methods. In one aspect, the acetabular guide 100 can be made of disposable plastic material.

The patient-specific acetabular guide 100 can also be used with a standard (non patient-specific) modular reamer 331 fitted with a patient-specific reamer adapter 360 to ream the acetabulum of the specific patient in pre-planned patient-specific orientations. This allows the acetabular implant 200 to be received in the selected anteversion and abduction orientations, as shown in FIG. 4H and discussed in connection with FIGS. 4A-4H.

Figures 4A, 4B:
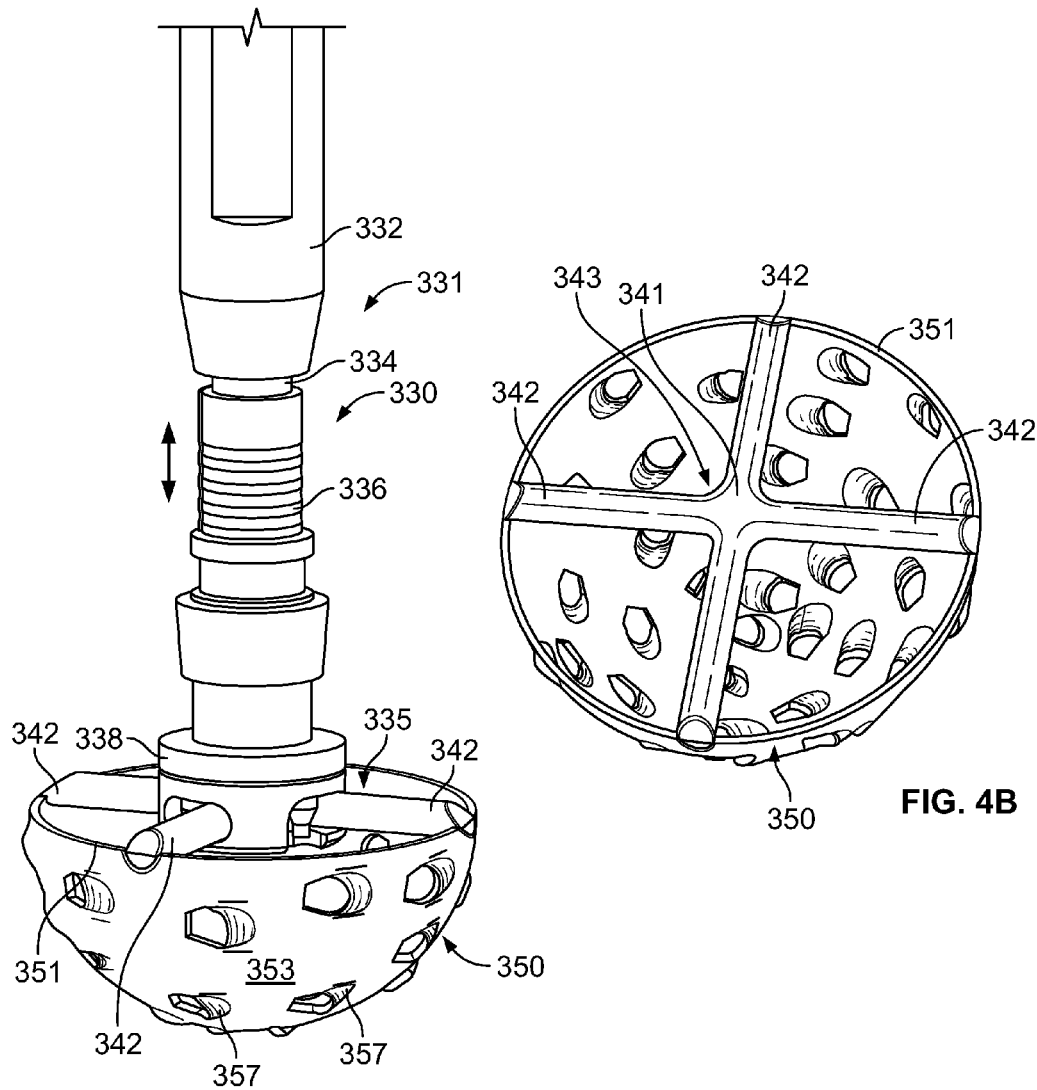
FIG. 4A is a perspective view of a modular reamer for use according to the present teachings.
FIG. 4B is bottom plan view of a reamer head of the reamer of FIG. 4A.
Figures 4C, 4D:
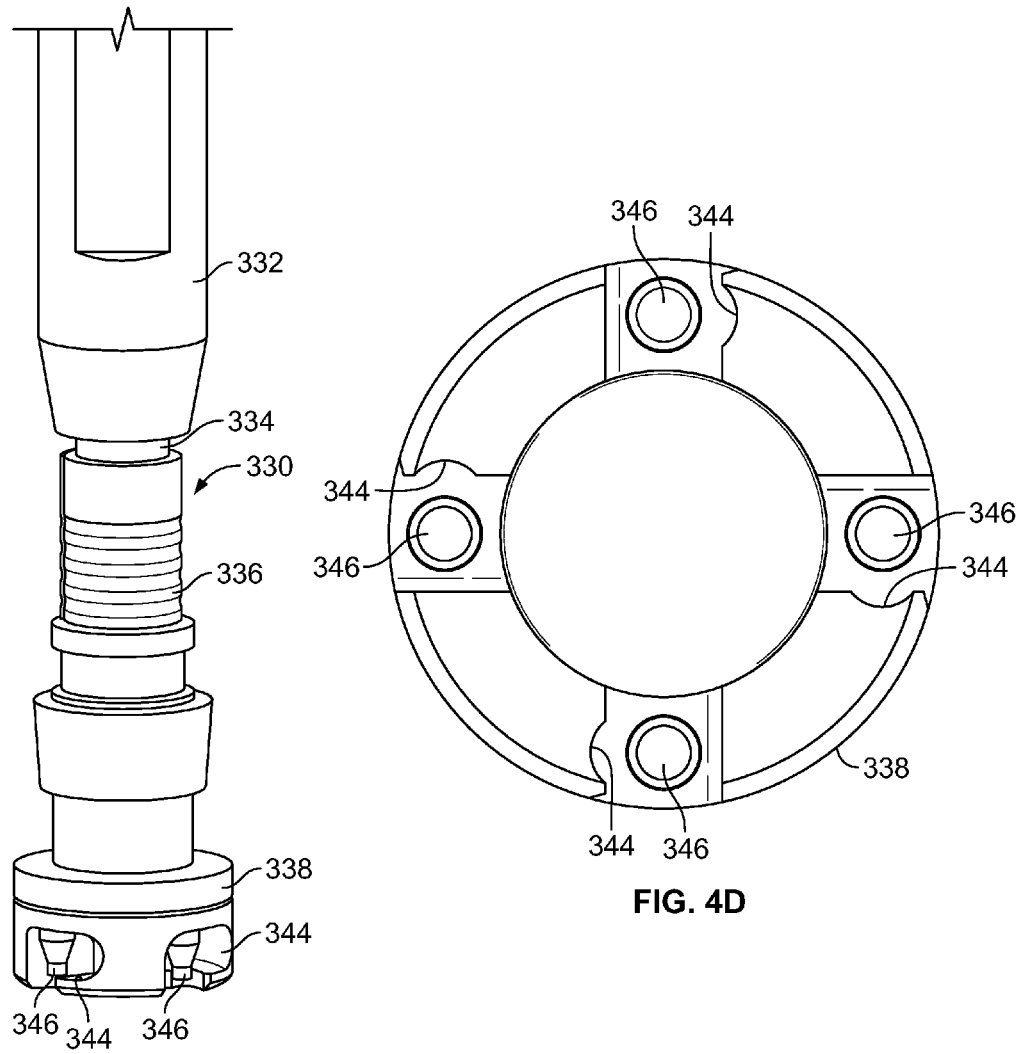
FIG. 4C is a perspective view of a reamer driver of the reamer of FIG. 4A.
FIG. 4D is bottom plan view of a distal end of the reamer driver of FIG. 4C.
Figure 4E:
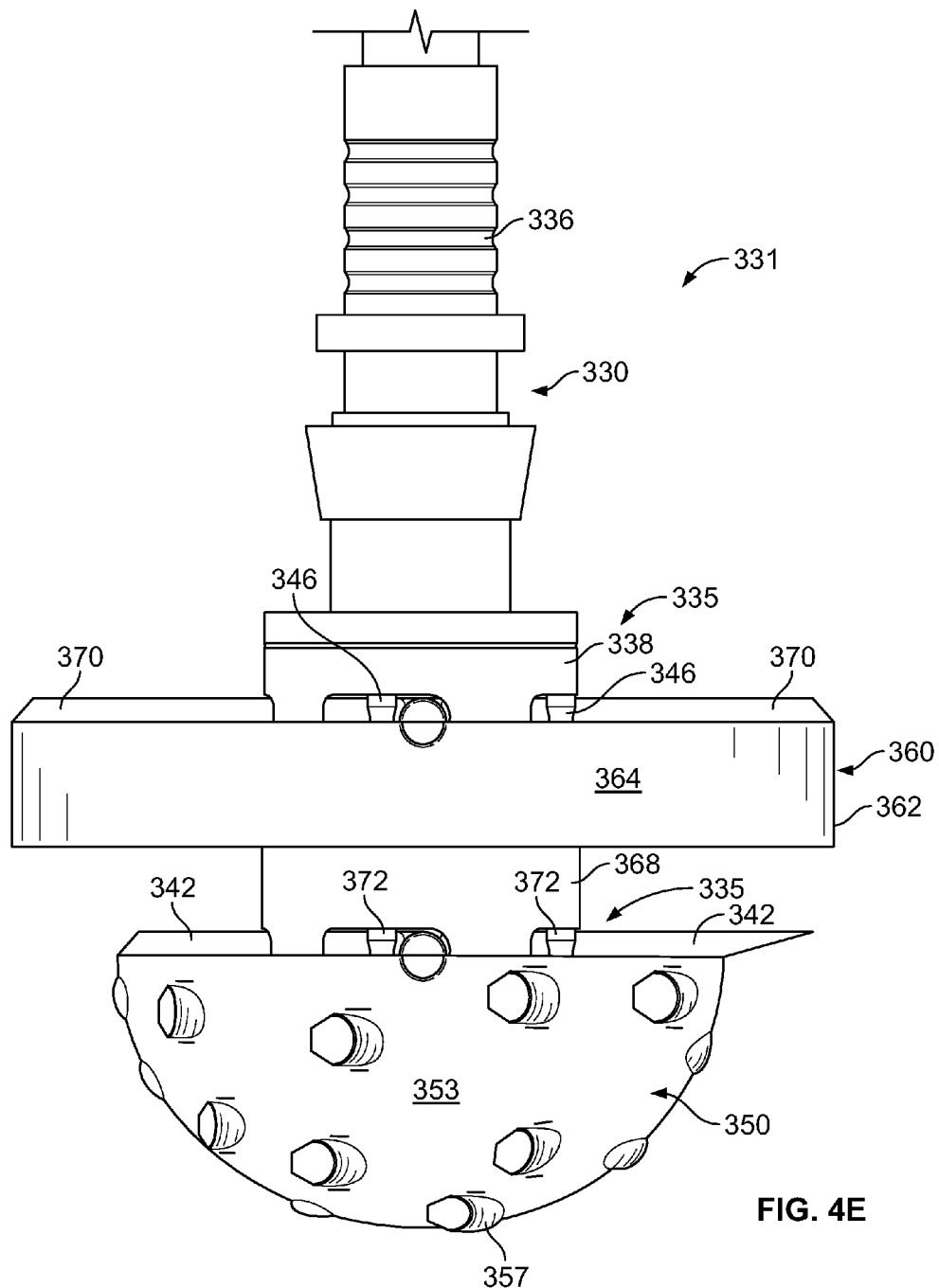
FIG. 4E is a perspective view of the modular reamer of FIG. 4A shown assembled with a an adaptor for use according to the present teachings.
Figure 4F:
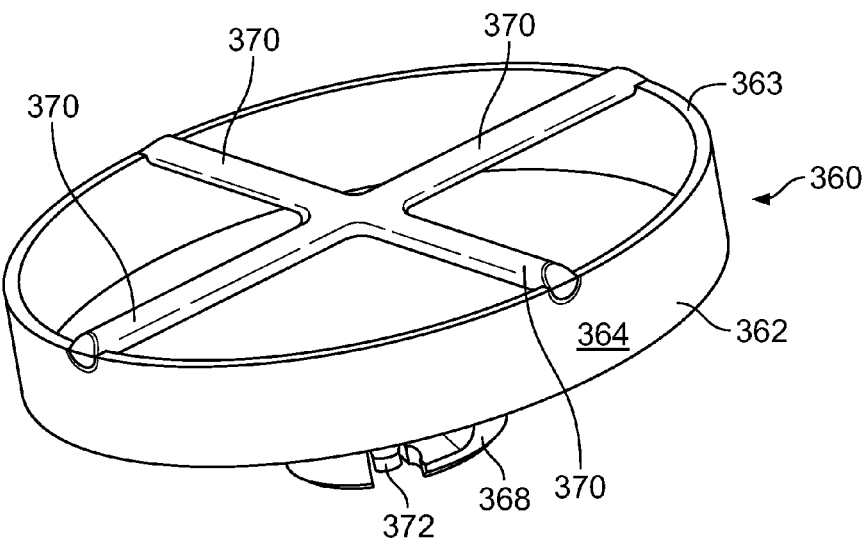
FIG. 4F is top plan view of the adaptor of FIG. 4E.
Figure 4G:
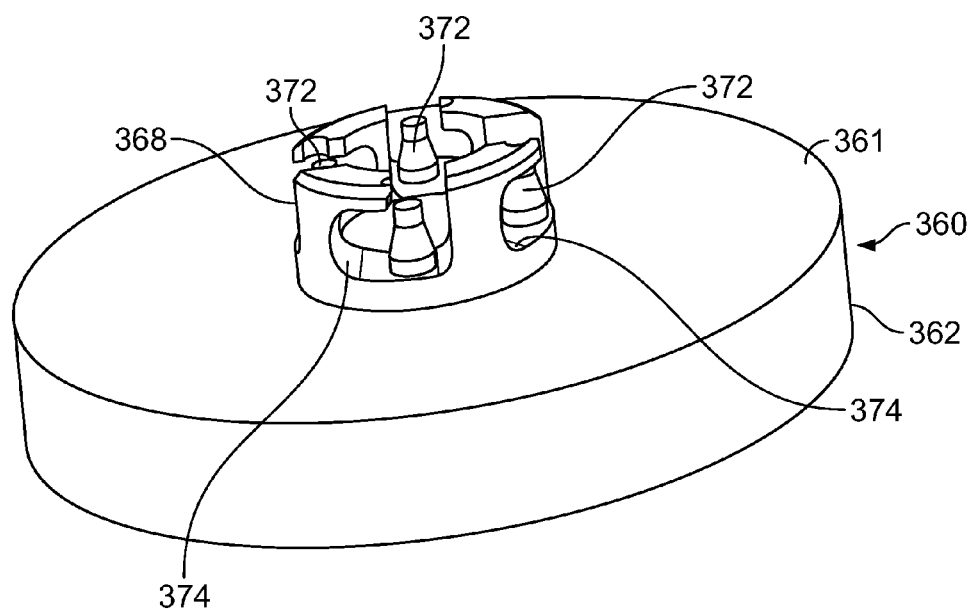
FIG. 4G is bottom plan view of the adaptor of FIG. 4E.
Figure 4H:
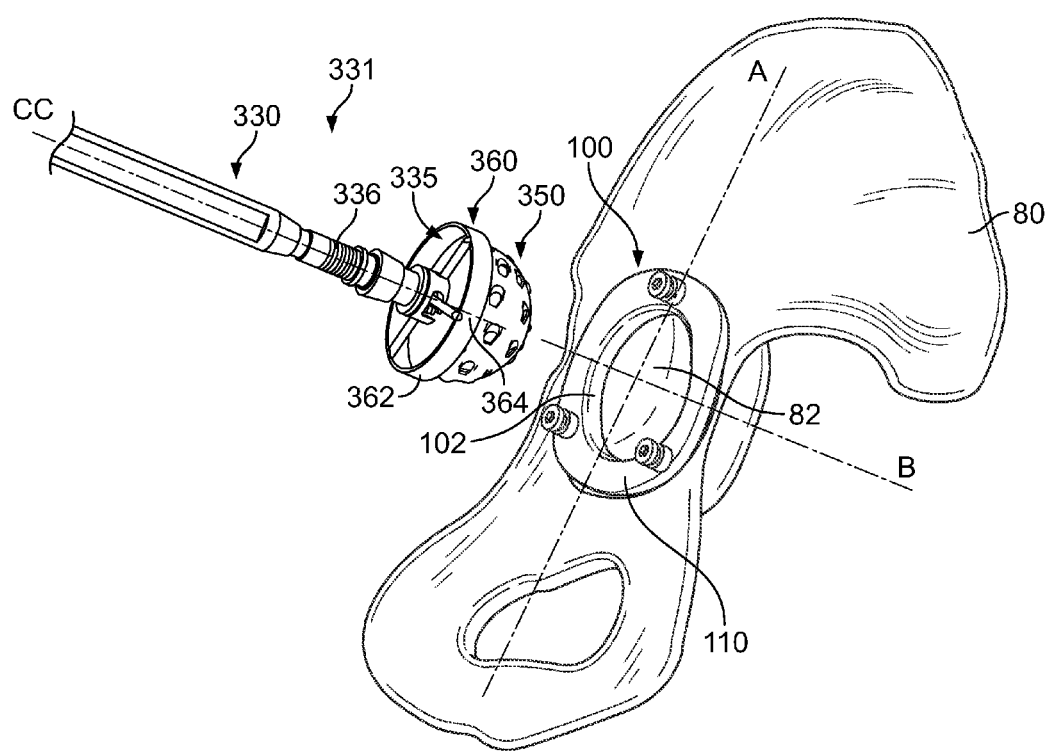
FIG. 4H is an environmental view of an assembled of a reamer with a patient-specific adapter according to the present teachings.

FIGS. 4A-4C illustrate an exemplary modular reamer 331 that includes a reamer driver 330 and a reamer head 350. The reamer driver 330 can be removably coupled to the reamer head 350 with a connecting mechanism 335, which can be a spring-loaded, or snap-fit or other type of releasable connection, including connections secured with a set screw or other easily removable fasteners. An exemplary quick-connect connection is illustrated in FIGS. 4A-4D and is also used to connect the reamer 331 to the reamer adapter 360, as illustrated in FIGS. 4E-4H.

The reamer head 350 can be in the form of a hollow cup with a semi-spherical reaming surface 353 bounded by a periphery 351. The reaming surface 353 defines a plurality of reaming formations or reaming teeth 357. A number of arms or rods 342 can be connected to the periphery 351 and form a first component of the quick-connect mechanism 335. The arms 342 can be attached to one another at a central hub 341 forming a frame 343, as shown in FIG. 4B.

The reamer driver 330 can include a handle or sleeve 332 receiving a driver shaft 334 for coupling to a driver tool at a proximal end (not shown) and having a distal connector 338. The distal connector 338 forms a second component of the quick connect mechanism 335, which is operated with a spring-loaded slider or trigger 336 coupled to the driver shaft 334. The distal connector 338 can include a number of openings or slots 344 and a corresponding number of movable or retractable pins 346. The number of slots 344 corresponds to the number of arms 342 and the slots 344 are sized and shaped to receive the arms 342. Although four arms, slots and pins are illustrated, a smaller or greater number can be used, for example two or three arms, slots and pins that can be evenly positioned radially about the reamer head 350. To connect the reamer driver 330 to the reamer head 350, the slots 344 are placed over the arms 342 with the pins 344 in their retracted position. The pins 344 can be retracted by moving the slider 336 in a direction away from the distal connector 338. When the slider 336 is released, the arms 342 are gripped between the pins 344 and the walls of the slots 344 and the reamer driver 330 is securely connected to the reamer head 350.

Referring to FIGS. 4E-4H, the patient-specific reamer adapter 360 can include can include a first portion 362 and a second portion 368. The first portion 362 can have an outer surface 364. The outer surface 364 can be, for example, cylindrical. The outer surface 364 can be shaped, sized and oriented to mate with the inner surface 102 of the patient-specific guide 100 to provide a selected and patient-specific anteversion angle about the first axis A and a selected abduction angle relative to the axis B, as shown FIG. 4H. In this respect, the outer surface 364 of the adapter 360 is patient specific.

The reamer adapter 360 can be coupled to the reamer with a quick-connect connection. For example, the reamer adapter 360 can be coupled between the reamer driver 330 and the reamer head 350 with corresponding components of the quick-connect mechanism 335 used for the connecting the reamer driver 330 to the reamer head 350. Referring to FIGS. 4E-4H, the first portion 362 can include a number of arms 370 coupled to a proximal periphery 363 of the first portion 262 and are configured to engage the distal connector 338 of the reamer driver 330, i.e. to be gripped in corresponding slots 344 by corresponding pins 346. In this regard, the arms 370 of the first portion 362 provide a component that is complementary to the quick-connect component of the reamer driver 330 and complete a quick-connect mechanism 335 between the reamer drier 330 and the reamer adapter 360.

Similarly, the second portion 368 of the reamer adapter 360 can include a quick-connect component complementary to the quick-connect component of the reamer head 350 to complete the quick-connect mechanism 335. More specifically, the second portion 368 can include a number of slots 374 and pin 372 for gripping the arms 342 of the reamer head 350. Accordingly, the same type of quick-connect mechanism 335 that is used to couple the reamer driver 330 to the reamer head 350 can be used to couple the reamer adapter 360 between the reamer driver 330 and the reamer head 350, as illustrated in FIGS. 4A and 4E. It is noted that the quick-connect mechanism 335 is not limited to the exemplary embodiment illustrated, but can be any quick-connect mechanism used for non-patient-specific modular reamers, include snap-fit, tapered connectors, threaded connectors, or any other connectors with complementary components "a" for the reamer driver 330 and "b" for the reamer head 350, which are then used in reverse order to couple the reamer adapter 360 therebetween in a sequence a-b-a-b. In the illustrated quick-connect mechanism 335, component "a" includes slots and pins and component "b" includes arms.

Referring to FIG. 4H, the assembled reamer 331 with the patient-specific adapter 360 can be used with the patient-specific acetabular guide 100 to ream the acetabulum 82 of the patient to receive an implant in a selected patient-specific orientation according to the pre-operative plan. As described above in relation to FIGS. 1-4, the acetabular guide 100 is attached to the acetabulum 82 in only one position, such that the inner surface 102 provides an orientation guide for the reamer head 350. In particular, the outer surface 364 of the reamer adapter 360 mates in a complementary close-fit manner with the inner surface 102 of the acetabular guide 100, such that the reamer head 350 can be oriented as specified in the pre-operative plan to ream the acetabulum in the selected anteversion and abduction orientations relative to the corresponding axes A and B. After the acetabulum 82 is reamed, the acetabular implant 200 can be impacted in the same selected orientation using the inserter/impactor 300 discussed in connection with FIGS. 2 and 3.

The exemplary acetabular guide 100 illustrated in FIGS. 1A, 2 and 4H is annular for placement around the acetabulum 82. In other embodiments, an acetabular guide 400 positioned only in a portion around the acetabulum 82 can also be used. Referring to FIGS. 5-10, the patient-specific acetabular alignment guide 400 and other instruments for guiding an acetabular implant are illustrated. The patient-specific acetabular alignment guide 400 can be prepared during a pre-operative plan for the surgical procedure based on a three-dimensional image of the relevant anatomy of the patient including portions of the pelvis 80, the acetabulum 82, the acetabular rim area 84, the periacetabular area and generally the hip joint of the patient. The three-dimensional image of the anatomy of the patient can be developed by commercially available software, as discussed above, using MRI, CT, X-rays or other scans of the particular patient.

Figure 5:
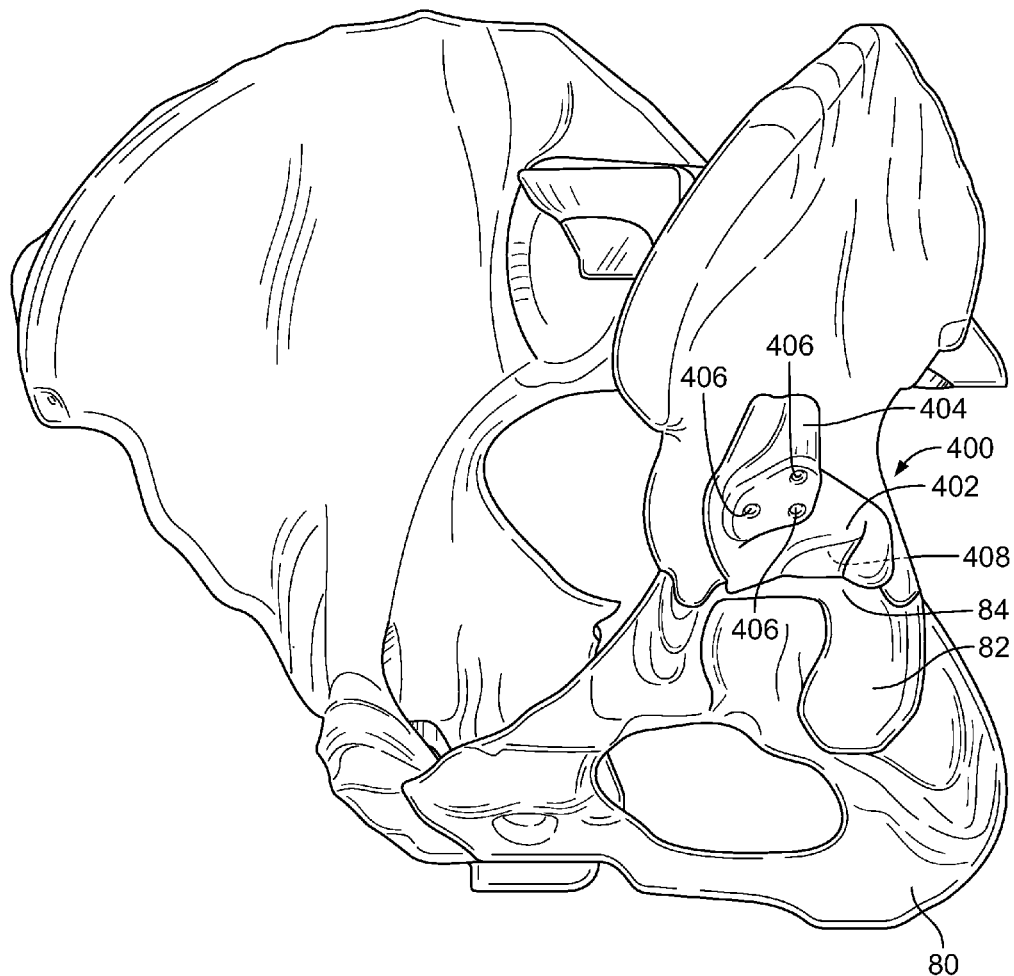
FIG. 5 is a perspective environmental view of an exemplary acetabular alignment guide according to the present teachings.
Figure 6:
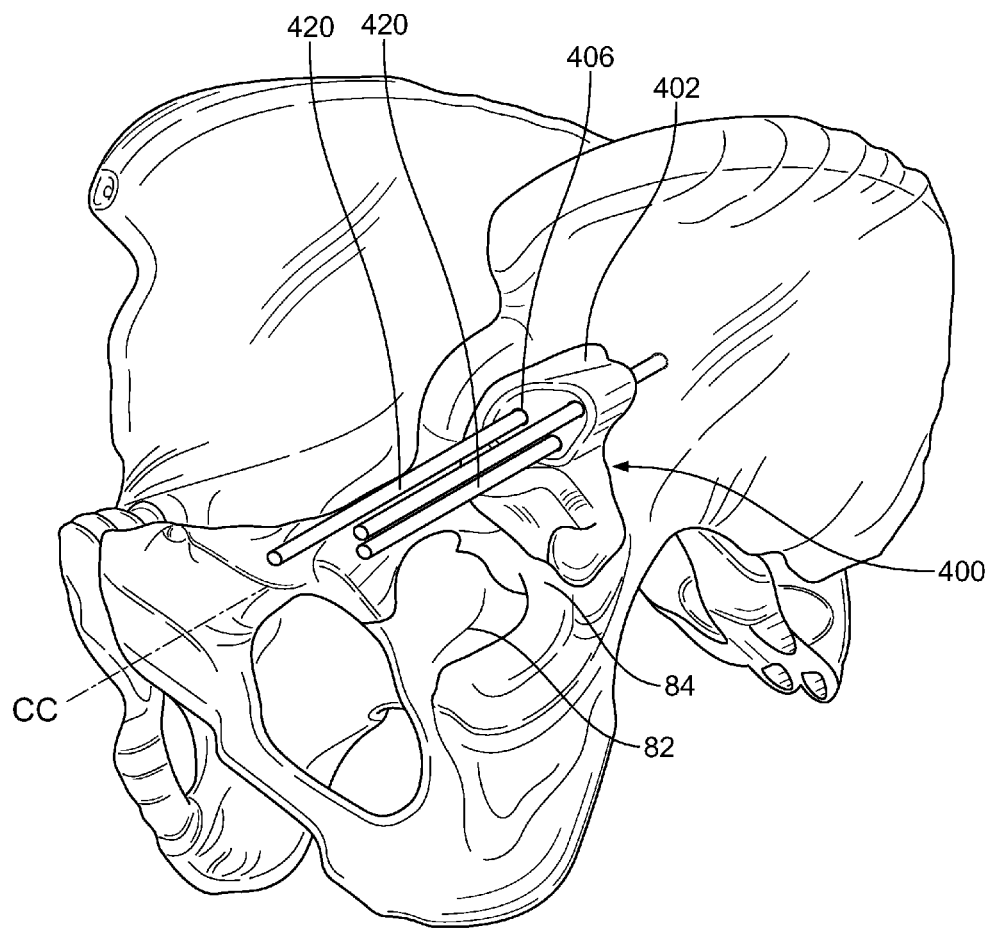
FIG. 6 is a perspective environmental view of the acetabular alignment guide of FIG. 5 shown with a plurality of guiding pins.

Referring to FIGS. 5 and 6, the acetabular alignment guide 400 can include a first portion 402 configured and adapted to be positioned around the rim surface 84 of the acetabulum 82 and a second portion 404 configured and adapted to be positioned around the periacetabular area of the pelvis 80 of a specific patient. The acetabular alignment guide 400 can include a three-dimensional curved patient-specific bone engagement surface 408. The bone engagement surface 408 is defined to match complementarily to a portion of the acetabular rim surface 84 and a portion of an adjacent periacetabular area of the pelvis 80 of the patient for close contact/nesting thereon in only one position and orientation. The second portion 404 of the acetabular alignment guide 400 is designed during the pre-operative plan to define a plurality of elongated through-slots, apertures or other guiding formations 406 directed toward the periacetabular area for guiding a plurality of alignment pins 420 parallel to an acetabular centering axis CC, the location and orientation of which is determined according to the preoperative plan for the specific patient. The second portion 404 can be reinforced with additional materials and/or have thicker dimensions for stability.

Figure 7:
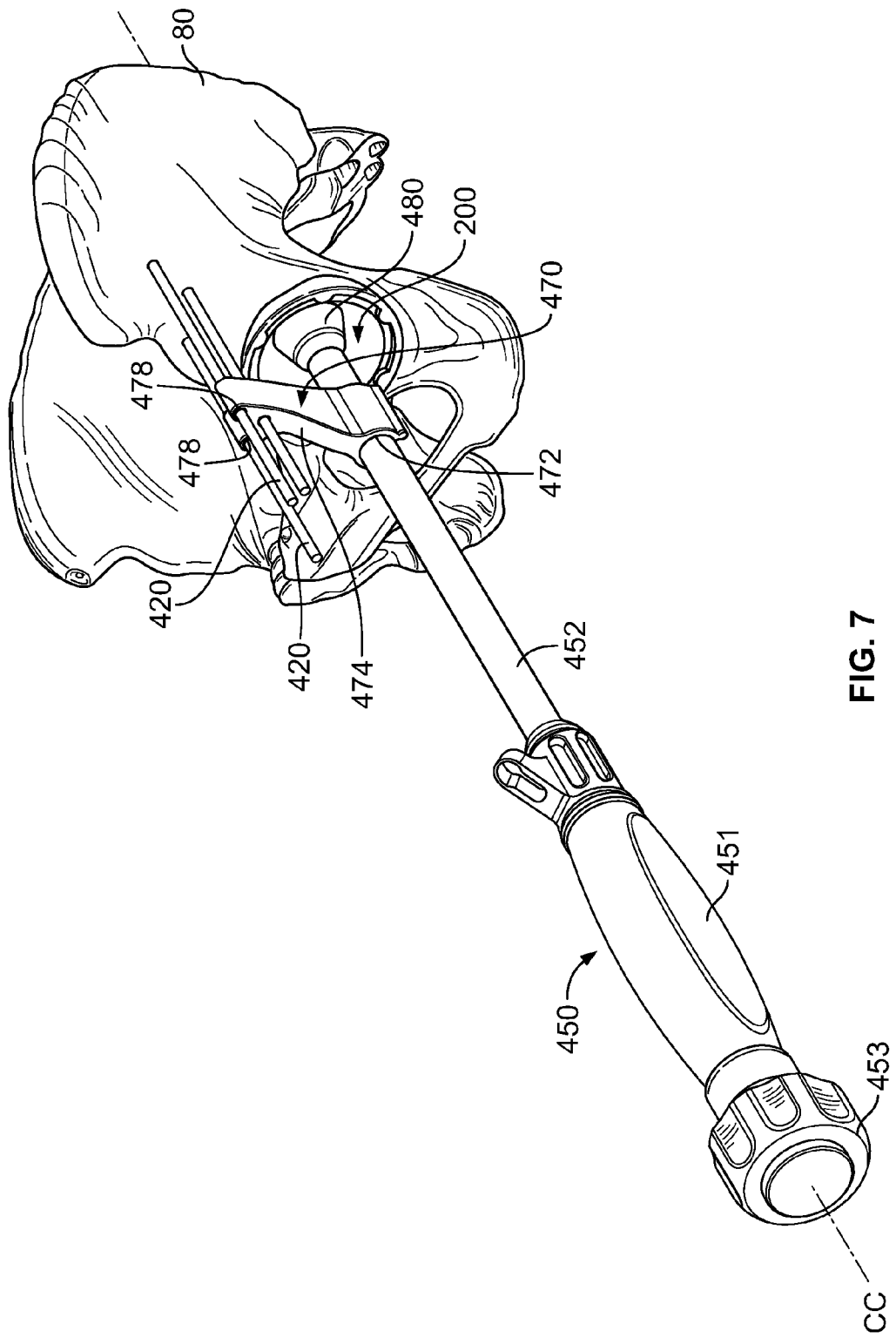
FIG. 7 is a perspective environmental view illustrating inserting an acetabular cup with an instrument guided by the guiding pins of FIG. 6.
Figure 8:
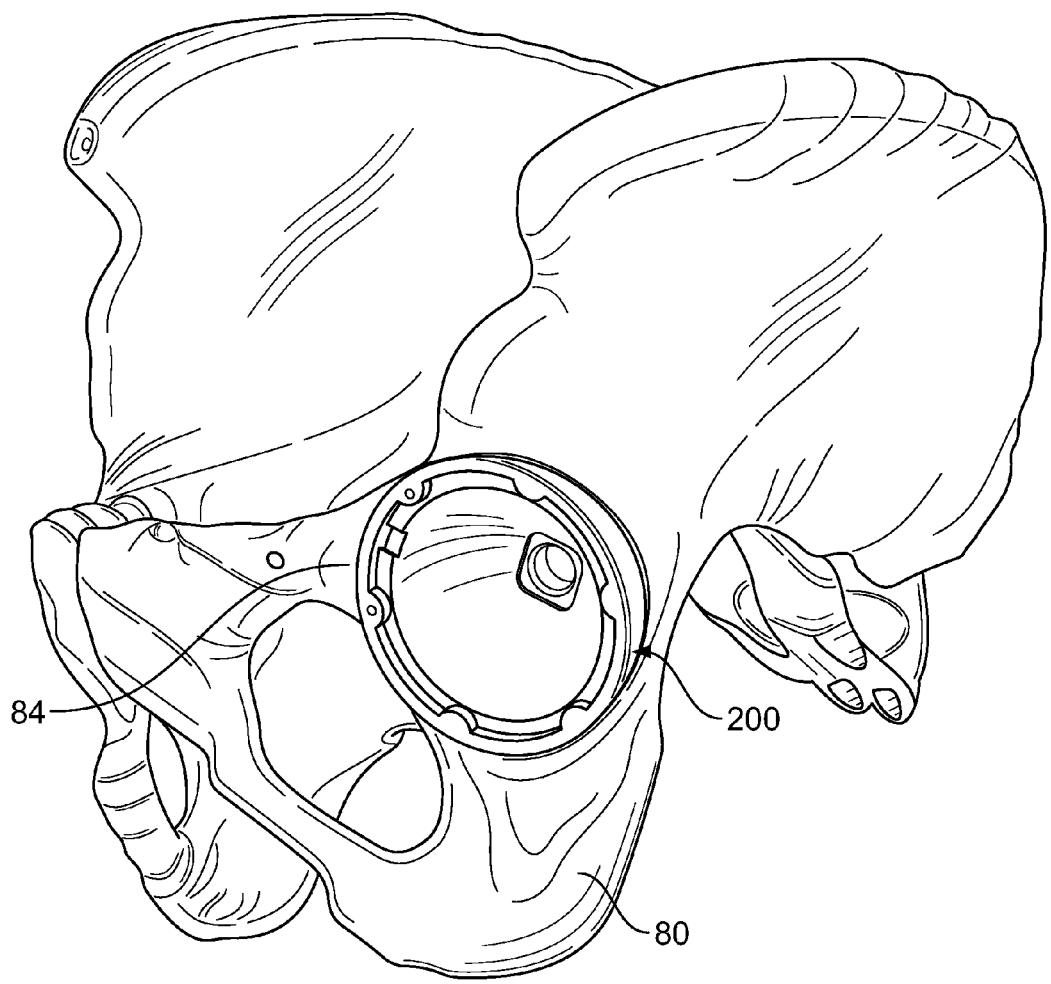
FIG. 8 is a perspective environmental view of an exemplary acetabular implant.

Three guiding formations 406 in the form of through holes and a corresponding number of alignment pins 420 are illustrated in FIGS. 5 and 6. Depending on the patient and/or procedure, a different number of guiding formations 406 and alignment pins 420 can be used. The alignment pins 420 can be parallel defining a patient specific orientation and operable for locating the acetabular centering axis CC. The alignment pins 420 can removably guide along the same axis other instruments associated with the insertion of an acetabular implant 200 after the acetabular alignment guide 400 is removed, as shown in FIG. 7, for example. The orientation and location of the guiding formations 406 can be patient-specific and determined pre-operatively to facilitate guiding and supporting the various instruments used for positioning, inserting and impacting the acetabular implant 200, as discussed below.

Referring to FIG. 7, after the alignment pins 420 have been inserted into the bone, the acetabular alignment guide 400 can be removed. An acetabular positioner or inserter or inserter/impactor 450 can be guided by the alignment pins 420 for inserting the acetabular implant 200 in the acetabulum. The inserter 450 can include a handle 451 with a knob 453 and a shaft 452 coupled to a patient-specific alignment adapter 470. The patient-specific alignment adapter 470 can include an arm 474 defining a plurality of alignment apertures 478 complementary to the alignment pins 420, such that the alignment adapter 470 can removably slide over the alignment pins 420. In this respect, the shape and size of the arm 474 and the placement, arrangement and configuration of the alignment apertures 478 can be determined during the pre-operative plan to correspond to the guiding formations 406 of the acetabular alignment guide 400. The alignment adapter 470 can include a coupling opening 472 for removably receiving the shaft 452 of the inserter 450 or can be integrally coupled to the shaft 452 of the inserter 450. The coupling opening 472 can be, for example, an interference fitting or snap-on side slot. Alternatively, the coupling opening 472 can be an enclosed hole, which receives the shaft 452 of the inserter 450, when the shaft is modularly coupled to the inserter 450. The inserter 450 can be connected to and disconnected from the acetabular implant 200 with a coupler 480 at the distal end of the shaft 452 by rotating the knob 453. The coupler 480 can also be modularly connected to the shaft 452. During insertion of the acetabular implant 200, the alignment pins 420 help stabilize, guide and secure the orientation of the inserter/impactor 450 and acetabular implant 200 and place the acetabular implant 220 in the desired position and orientation relative to the acetabulum 82 as determined during the pre-operative plan using imaging scans of the patient.

Figure 9:
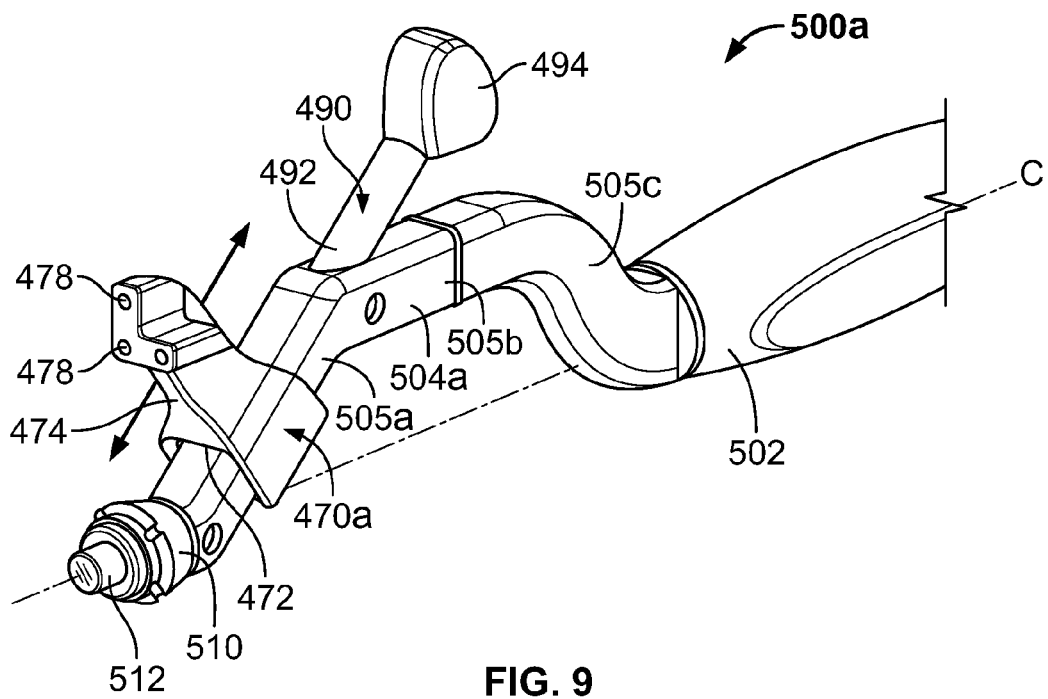
FIG. 9 is a perspective view of an exemplary impactor according to the present teachings.
Figure 10:
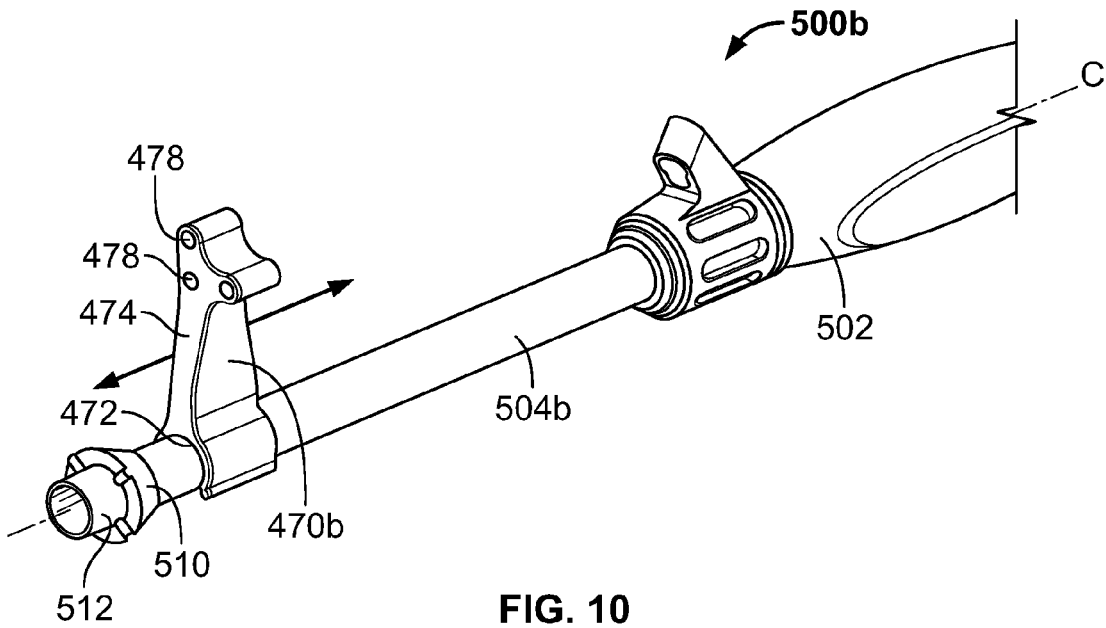
FIG. 10 is a perspective view of an exemplary offset impactor according to the present teachings.

Similar patient-specific alignment adapters 470 can be used for guiding other type of inserters or impactors or reamers with reamer driver handles or other instruments, such as, for example, reamers and impactors that can be used during the preparation and implantation procedure. Referring to FIGS. 9 and 10, first and second impactors (or other acetabular instruments) 500a, 500b are illustrated with respective first and second patient-specific alignment adapters 470a, 470b. The first impactor 500a is an offset impactor 500a generally used for minimally invasive procedures, and the second impactor 500b is straight, non-offset impactor. Each of the first and second impactors 500a, 500b can be modular and include a handle 502 respectively coupled to a first shaft 504a or second 504b terminating at a coupler 510 with an end connector 512. The first shaft 504a of the first impactor 500a is offset relative to a longitudinal axis C (designed to coincide with the acetabular centering axis CC) passing through the handle 502 and the end connector 512. The shaft 504b of the second impactor 500b is coaxial with the handle 502.

As illustrated in FIG. 9, the offset first shaft 504a can include a center portion 505c offset and substantially parallel to the longitudinal axis C and first and second end portions 505a, 505b angled relative to the center portion 505c for defining the offset. The first end portion 505a can be cannulated or hollow for receiving a shaft 492 of a driver 490 coupled to the end connector 512, such that the end connector 512 can be secured to the acetabular implant 200 by rotating a knob 494 of the driver 490. The first alignment adapter 470a includes a coupling opening 472 (enclosed hole or side opening/slot) through which the portion 505a can pass through. As discussed above in connection with alignment adapter 470 and the inserter 450 of FIG. 7, the shape and size of the arm 474 and the placement and arrangement/configuration of the alignment apertures 478 can be determined during the pre-operative plan to correspond to the guiding formations 406 of the acetabular alignment guide 400 and the location and orientation of the alignment pins 420, such that the parallel alignment pins 420 can pass through the parallel alignment apertures 478 to guide the first impactor 500a relative to the acetabular implant 200 and relative to the acetabulum 82. The first alignment adapter 470a can be removably coupled to the first impactor 500a and can be slidably adjusted in position relative to the first portion 505a while maintaining the alignment orientation of the alignment apertures 406 relative to axis CC and the alignment pins 420.

Referring to FIG. 10, the second impactor 500b can be used similarly. Because the shaft 504b is substantially straight (not offset), the end connector 512 can be attached to the acetabular implant 200 by simply rotating the handle 502 or a knob attached to the handle (not shown), similarly to the inserter 450 shown in FIG. 7. Each impactor 500a, 500b can be modular, such that the handle 502, the shaft 504a, 504b and/or the coupler 510 can be disassembled for removably mounting the alignment adapter 470a, 470b. Additionally, or alternatively, the coupling opening 472 can be a snap-on side opening or side slot for removably receiving the alignment adapter 470a, 470b without disassembling the impactor 500a, 500b.

In some embodiments, the same alignment adapter can be used for more than one conventional acetabular instrument. For example, the same the alignment adapter 470 (or 470b) can be used optionally either with the inserter/impactor 450 or the impactor 500b, or with an acetabular reamer, such as reamer 331.

It will be appreciated from the above discussion, that although the patient-specific acetabular alignment guide 400 has an engagement surface 408 that is complementary to the acetabular/periacetabular area of the patient, the alignment adapters 470, 470a and 470b may or may not have a patient-specific engagement surface as they are at a distance away from the bone surface during use. Rather, the location and arrangement of the alignment apertures 478 on the arm 474 is patient-specific, such that the corresponding alignment adapter 470, 470a, 470b can be mounted over the plurality of the alignment pins 420 that have been already secured around the acetabulum 82 of the patient using acetabular alignment guide 400.

The acetabular alignment guide 400 and the alignment adapters 470, 470a, 470b can be made of disposable polymeric materials or any other biocompatible materials. The alignment adapters 470, 470a, 470b can be used with acetabular inserters, positioners, reamers, impactors and other instruments used during the acetabular procedure. The acetabular alignment guide 400 and one or more alignment adapters 470 can be provided in a form of a kit with a set of alignment pins 420. Other reusable, non custom instruments can be also included, for example, an inserter, reamer impactor, etc. The kit can include an acetabular implant 200, which can be custom-made or non custom-made, as approved and selected by the surgeon.

Figure 11A:
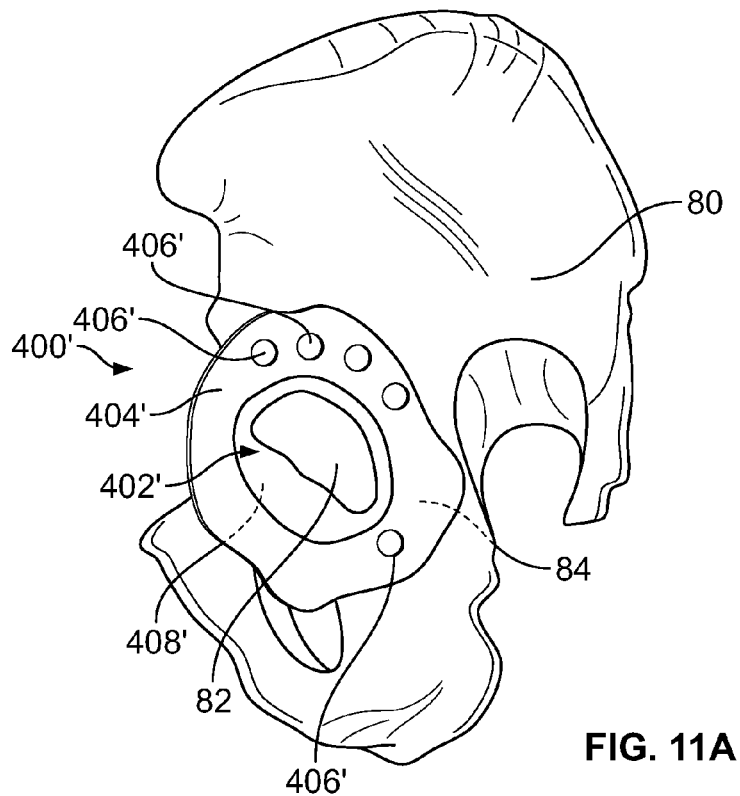
FIG. 11A is an environmental view of a patient-specific acetabular guide according to the present teachings.
Figure 11B:
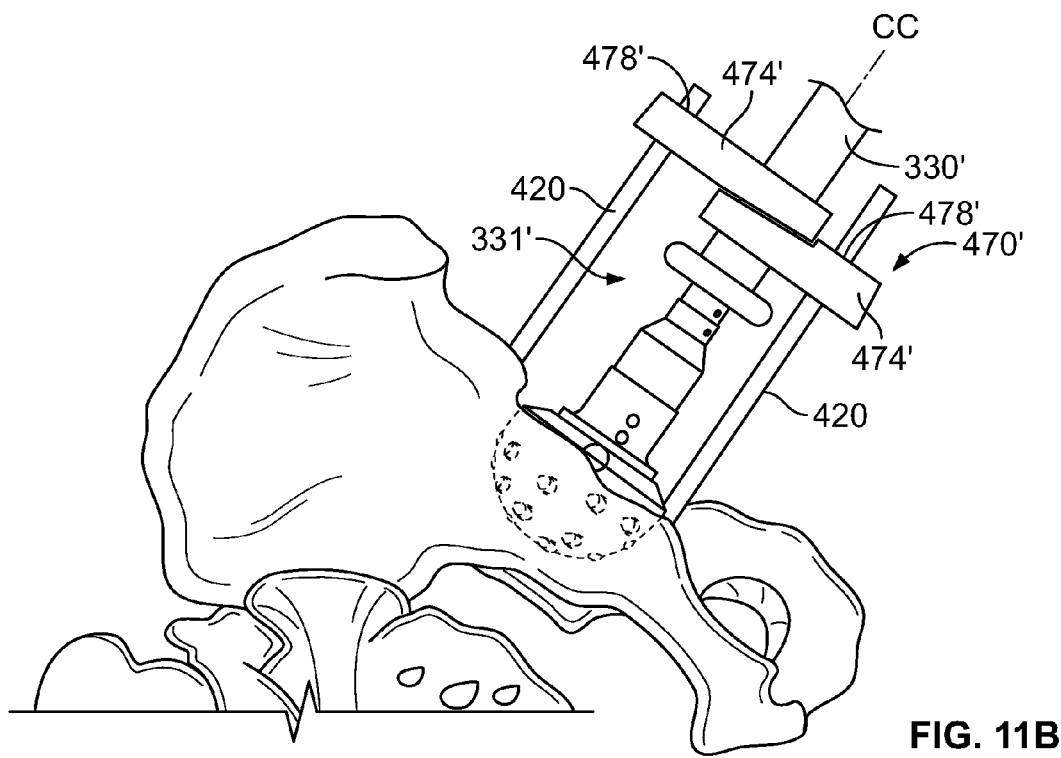
FIG. 11B is an environmental view of a reamer patient-specific adapter guided for reaming the acetabulum by alignment pins placed using the patient-specific acetabular guide of FIG. 11A.
Figure 11C:
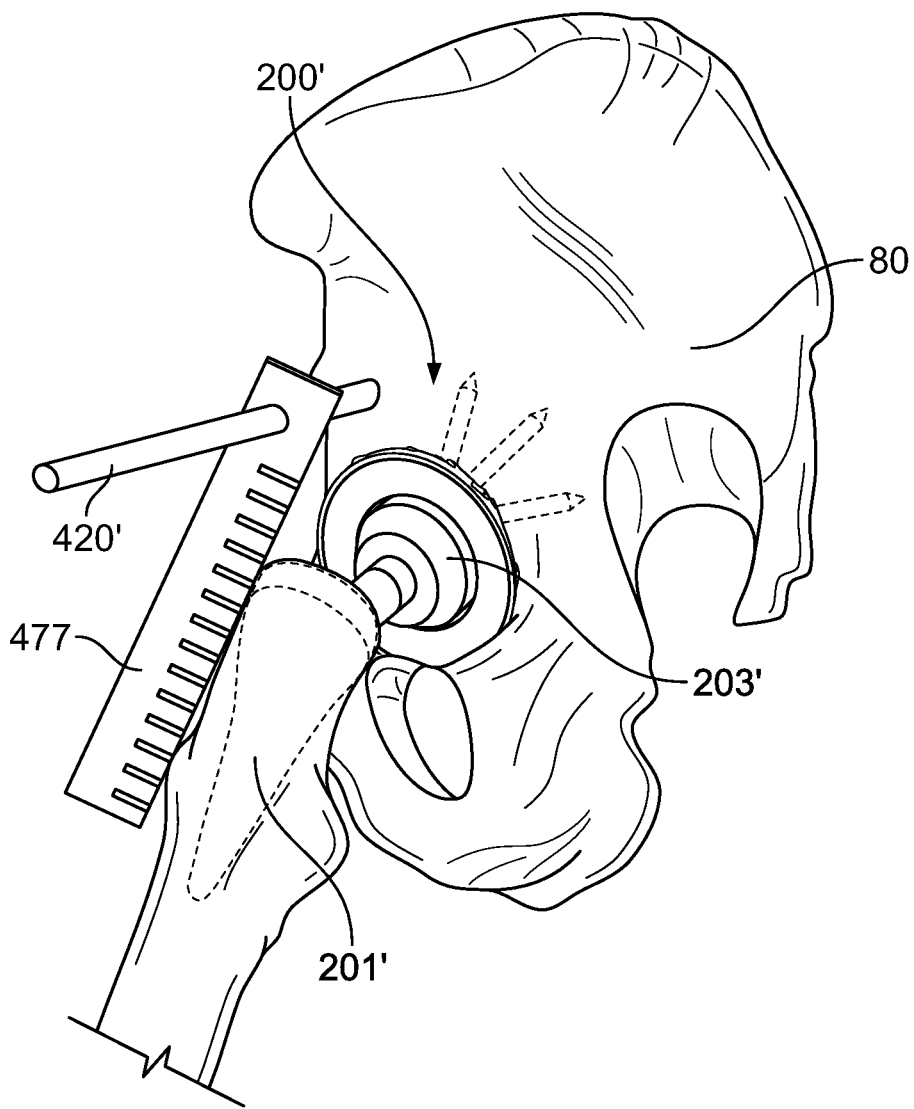
FIG. 11C is an environmental view of a length scale for measuring a length of an implant, the scale guided by an alignment pin placed using the patient-specific acetabular guide of FIG. 11A.
Figure 12:
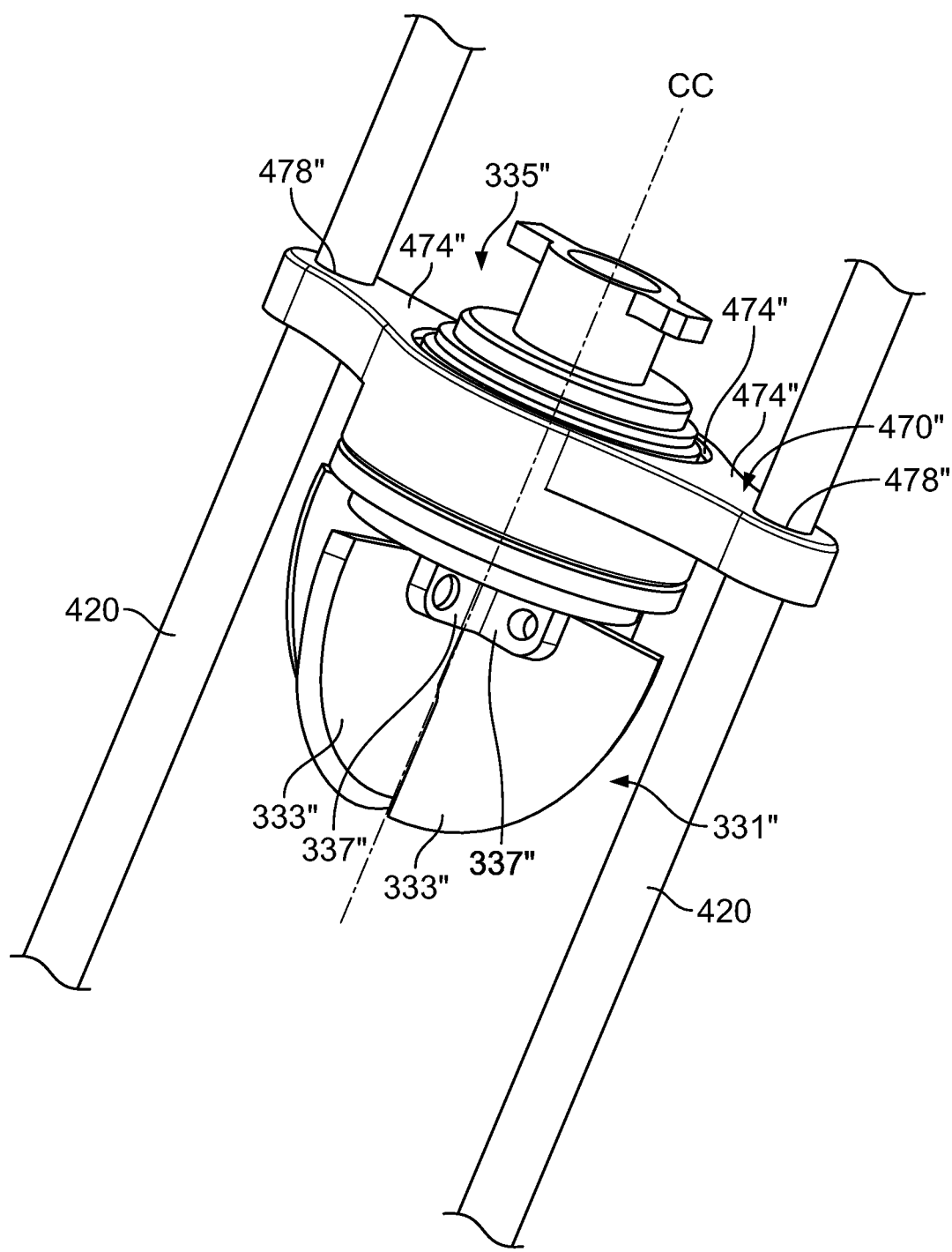
FIG. 12 is a perspective view of a reamer with a patient-specific adapter guided for reaming the acetabulum by alignment pins placed using the patient-specific acetabular guide of FIG. 11A.

Referring to FIGS. 11A to 12, another patient-specific acetabular guide 400' is illustrated for use with a reamer 331'. As discussed above in connection with acetabular guides 100 and 400, the acetabular guide 400', can include a first portion 402' configured and adapted to be positioned around the rim surface 84 of the acetabulum 82 and a second portion 404' configured and adapted to be positioned around the periacetabular area of the pelvis 80 of a specific patient. The acetabular alignment guide 400' can include a three-dimensional curved patient-specific bone engagement surface 408', which is the underside surface of the first and second portions 402', 404' that nestingly mates with the specific patient's anatomy. In the exemplary embodiment illustrated in FIG. 11A, the first portion 402' can extend around the entire inner rim surface 84 of the acetabulum and at least a portion of the acetabulum 82. Similarly, the second portion 404' can extend around the entire periacetabular area around the acetabulum 84 when additional stability and attachment area is desired for the particular patient or preferred by the surgeon. The bone engagement surface 408' can be designed to match complementarily to portions of the acetabular rim surface 84, of the acetabulum 82 and of an adjacent periacetabular area of the pelvis 80 of the patient for close contact/nesting thereon in only one position and orientation. The second portion 404' of the acetabular alignment guide 400 is also designed during the pre-operative plan to define a plurality of elongated through-slots, apertures or other guiding formations or holes 406' directed toward the periacetabular area for guiding a plurality of alignment pins 420 parallel to the pre-determined acetabular centering axis CC, as discussed above in connection with FIGS. 5-7. After the alignment pins 620 are secured to the bone, the acetabular guide 400' can be removed leaving the alignment pins 420 for use with a reamer, as discussed below.

A reamer 331' or 331" can be guided by the alignments pins 420, as shown in FIGS. 11B and 12, respectively, along the acetabular centering axis CC. An off-the-shelf or standard (non custom) reamer 331', 331" can be used in combination with an adjustable or a patient-specific adapter 470', 470". The adapter 470' can include one or more arms 474' (two arms 474' are illustrated in FIG. 11B). Each arm 474' can be coupled to a shaft 330' of the reamer 431' with a quick-coupling arrangement 474', which can be, for example, an opening in the arms configured for receiving the shaft 330' or other coupler. Each arm 474' can include at least one opening 478' positioned and configured for receiving a corresponding alignment pin 420, which is secured to the bone in a predetermined position and orientation using the patient-specific alignment guide 400' through a corresponding hole 406 of the guide 400". Accordingly, the location and orientation of the openings 478' on the arms 474' and relative to the acetabular centering axis CC are patient-specific. In some embodiments, an arm 474' can include more than one opening 478'. The arms 474' can be integrally attached to one another, or modularly or separately coupled to the shaft 330'. One of the alignment pins, pin 420' for example, can provide a fixed point of reference for measuring the length of the leg of the patient for determining the length of an implant 200' and the depth in the corresponding intramedullary canal. The implant 200' can include a head 203' and a stem 201', as shown in FIG. 11C. A scale or other measuring device 477 can be coupled to the pin 420' for measuring the length and sizing the implant 200'. The scale 477 can be slidably placed over the pin 477' as shown in FIG. 11B. The length can be measured before implantation and also-post implantation (as shown in FIG. 11B) for confirming proper impaction and placement of the implant.

Referring to FIG. 12, a non-custom reamer 331" can be coupled with a patient-specific adapter 470" designed to slide over the alignment pins 420, after the alignment pins 420 are secured on the patient's pelvis 80 in a patient-specific configuration, position and orientation, which also determines the acetabular centering axis CC, as discussed above in connection with FIGS. 5-7. In the embodiment illustrated in FIG. 12, the adapter 470" can be monolithic and include two arms 474" for receiving respectively two alignment pins 420 through corresponding openings 478", although different number of arms 474" can be used and each arm 474" can include more than one opening 478" for receiving more than one pin 420. The adapter 470" can by coupled to the reamer 331" with a quick-connect to the shaft of the reamer 331", as described above in relation to FIGS. 4A-4G, or with another type of connection 335", such as snap-fit or threadable socket or bayonet coupling. The reamer 331" can be of the blade type, including reaming blades 333". In one embodiment, the blades 333" can be removable, replaceable and/or disposable. Each blade 333" can be semicircular or quarter-circular and can be attached to a chuck or other support 337" of the reamer 331" with set screws or grooves or jaws.

Figure 13:
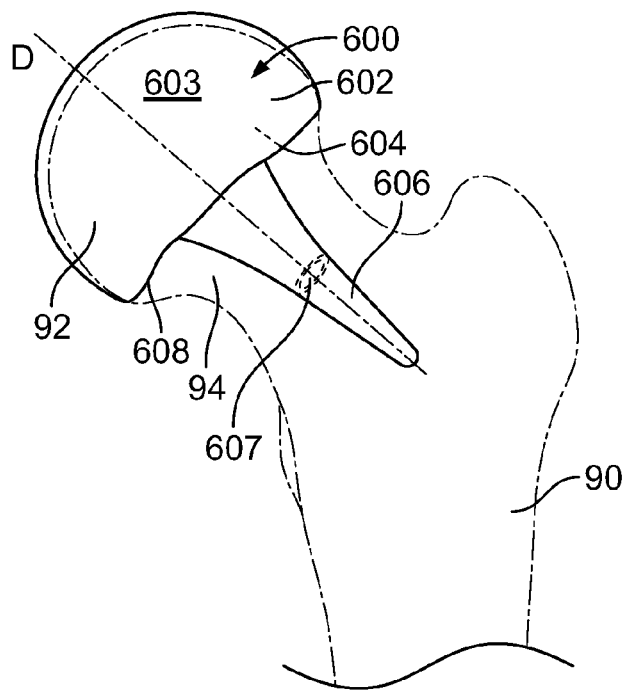
FIG. 13 is an environmental view of a patient-specific resurfacing femoral implant according to the present teachings.
Figure 14A:
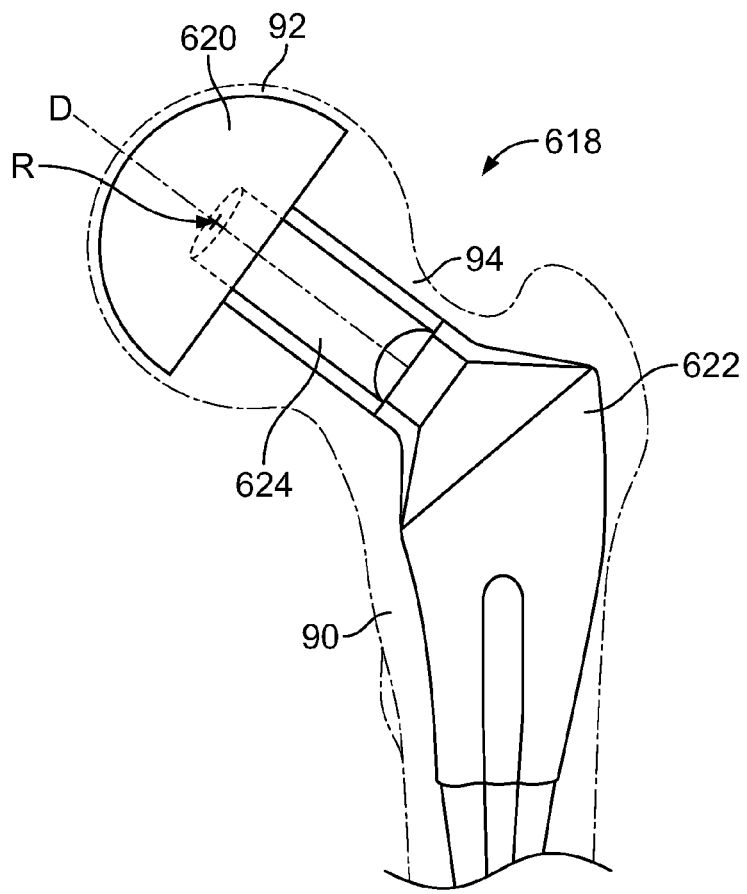
FIG. 14A is an environmental anterior view of a patient-specific femoral implant according to the present teachings.
Figure 14B:
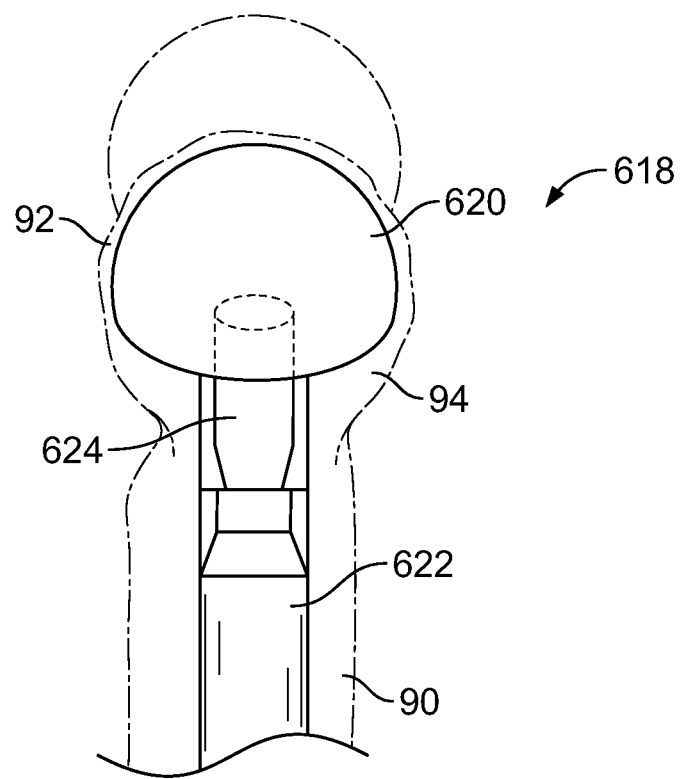
FIG. 14B is an environmental anterior view of the femoral implant of FIG. 14A.

In some procedures, the acetabular implant 200 discussed above can be used to articulate with a patient-specific resurfacing or replacement proximal femoral component, as shown in FIGS. 13, 14A and 14B. For example, a patient-specific resurfacing implant can be designed during the pre-operative plan based on image models reconstructed from scans of the patient.

Referring to FIG. 13, when the femoral head 92 is salvageable and need not be resected and replaced, the diseased or defective surface of the femoral head 92 can be identified in the image. A femoral component 600 can be designed to replace the defective portions, such as poor bone quality and/or avascular regions of the femoral head 92. The femoral component 600 can include a dome-shaped portion or dome 602 with an outer convex articulating surface 603 for articulating with an acetabular implant or the patient's natural acetabulum and an inner bone engagement surface 604 that is designed to match and be complementary and match the surface of the femoral head 92 with or without soft tissue attached, as determined in the pre-operative plan. The dome 602 can have a periphery 608 designed such that the dome covers and resurfaces all the defective portions of the femoral head 92. The femoral component 600 can have a short stem 606, which is inserted through the femoral head 92 and secured into the femoral neck 94. The stem 606 can be designed during the preoperative plan based on the thee-dimensional reconstruction of the patient's anatomy from the patient's scans such that the axis of the stem D is placed in a selected position and orientation relative to the neck 94 of the patient's and in a selected anteversion orientation relative to the proximal femur 90. Additionally, the length of the stem 606 and the size and shape of the cross-section 607 along the length of the stem 606 can also be designed based on the preoperative plan and the reconstruction model of the neck 94 of the patient, such that bone preservation and adequate attachment support are balanced and/or optimized for the particular patient.

Referring to FIGS. 14A and 14B, a patient-specific femoral implant 618 for a proximal femur in which the femoral head 92 is resected can include a femoral head component 620, a femoral neck component 624 and a femoral stem component 622. The femoral implant 618 can be designed during the preoperative plan based on the thee-dimensional reconstruction of the patient's anatomy from the patient's scans such that the femoral head implant 620 and femoral neck component 624 cooperate to retain the axis D and the center of rotation R of the patient's femur or acetabulum, based on surgeon determination and preference. The femoral neck component 624 can be designed to match the patient's femoral neck 94 in size and orientation. The femoral stem implant 622 can be selected from standard (non custom) stem sizes) or can be customized for length, cross-section and/or shape for the specific patient.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An acetabular system comprising:
a patient-specific acetabular alignment guide including a bone engagement surface having first and second portions, the first portion configured and shaped to be conforming and complementary only to a portion of a rim surface around an acetabulum of a specific patient without extending into the acetabulum, and the second portion configured and shaped to be conforming and complementary to a periacetabular area outside the acetabulum of the specific patient in accordance with a three-dimensional model of the acetabulum of the specific patient reconstructed pre-operatively from an image scan of the patient, the acetabular alignment guide including a plurality of guiding formations extending through the second portion for guiding a plurality of alignment pins therethrough, wherein the plurality of guiding formations are arranged and configured based on a pre-operative plan for the patient.

2. The acetabular system of claim 1, further comprising a patient-specific alignment adapter couplable to an acetabular instrument, the alignment adapter including a plurality of apertures configured to correspond to the guiding formations of the acetabular alignment guide for sliding over the corresponding alignment pins.

3. The acetabular system of claim 2, wherein the plurality of guiding formations includes three guiding bores and the plurality of apertures of the patient-specific alignment adapter includes three corresponding apertures.

4. The acetabular system of claim 2, wherein the guiding formations are parallel guiding bores.

5. The acetabular system of claim 4, further comprising an acetabular inserter, the acetabular inserter including a shaft passing through a snap-on side opening of the alignment adapter.

6. The acetabular system of claim 4, further comprising an acetabular inserter, the acetabular inserter including a shaft removably coupled to the alignment adapter and parallel to the guiding bores.

7. The acetabular system of claim 4, further comprising an acetabular impactor, the impactor including a shaft removably coupled to the alignment adapter and having a handle that is offset relative to a central portion of the shaft of the impactor.

8. The acetabular system of claim 4, wherein the patient-specific alignment adapter has a patient-specific surface and is slidable relative to the acetabular instrument.

9. An acetabular system comprising:
a patient specific acetabular alignment guide including a bone engagement surface configured and shaped to be conforming and complementary to an acetabular and periacetabular area of an acetabulum of a specific patient in accordance with a three-dimensional model of the acetabulum of the specific patient and based on a preoperative plan, the acetabular alignment guide including a plurality of guiding formations extending therethrough for guiding a plurality of alignment pins in a periacetabular area of a patient;
an acetabular instrument including a handle, a shaft and an acetabular coupler; and
a first alignment adapter removably coupled to the shaft of the acetabular instrument, the first alignment adapter including a plurality of apertures configured to correspond to the guiding formations of the acetabular alignment guide, such that the alignment pins can pass through the apertures of the alignment adapter after the acetabular alignment guide is removed without removing the alignment pins from the patient.

10. The acetabular system of claim 9, wherein the shaft of the acetabular instrument is removably inserted through a coupling opening of the first alignment adapter.

11. The acetabular system of claim 10, wherein the coupling opening is a snap-on side opening.

12. The acetabular system of claim 9, further comprising a second acetabular instrument having a shaft removably couplable to the first alignment adapter.

13. The acetabular system of claim 9, further comprising:
an acetabular impactor having a handle and a shaft offset from the handle; and
a second alignment adapter removably coupled to the shaft of the acetabular impactor, the second alignment adapter including a plurality of apertures complementary to the guiding formations of the acetabular alignment guide, such that the alignment pins can pass through the apertures of the second alignment adapter after the acetabular alignment guide is removed without removing the alignment pins from the patient.

14. The acetabular system of claim 13, wherein the shaft of the acetabular impactor is removably inserted through a coupling opening of the second alignment adapter.

15. The acetabular system of claim 14, wherein the coupling opening is a snap-on side opening.

16. The acetabular system of claim 14, wherein the impactor is modular.

17. The acetabular system of claim 9, further comprising an acetabular implant.

* * * * *

UNITED STATES PATENT AND TRADEMARK OFFICE
CERTIFICATE OF CORRECTION

| | |
|---|---|
| PATENT NO. | : 8,603,180 B2 |
| APPLICATION NO. | : 13/111007 |
| DATED | : December 10, 2013 |
| INVENTOR(S) | : John R. White et al. |

Page 1 of 1

It is certified that error appears in the above-identified patent and that said Letters Patent is hereby corrected as shown below:

Title Page 9, References Cited, Other Publications, Column 2, line 51, (Information Disclosure Statement dated July 8, 2011, Form 1449, page 19, Non Patent Literature Documents, Reference No. CI2), Delete "Arthuroplasty" and insert --Arthroplasty--.

In the Specification
Column 3, Line 29; After "with", delete "a".
Column 6, Line 34; Delete "insert" and insert --inserter--.
Column 7, Line 39; Delete "insert" and insert --inserter--.
Column 7, Line 40; Delete "344" and insert --346--.
Column 7, Line 43; Delete "344" and insert --346--.
Column 7, Line 46; After "360", delete "can include".
Column 7, Line 53; After "shown", insert --in--.
Column 7, Line 63; Delete "262" and insert --362--.
Column 8, Line 3; Delete "drier" and insert --driver--.
Column 9, Line 59; Delete "220" and insert --200--.
Column 10, Line 3; After "impactor", delete "500a".
Column 10, Line 8; After "second", insert --shaft--.
Column 10, Line 38; Delete "406" and insert --478--.
Column 11, Line 13; After "reamer", insert --,--.
Column 11, Line 34; Delete "84" and insert --82--.
Column 11, Line 47; Delete "620" and insert --420--.
Column 12, Line 12; Delete "477'" and insert --420'--.
Column 12, Line 13; Delete "FIG. 11B" and insert --FIG. 11C--.
Column 12, Line 14; Delete "also-post implantation" and insert --also post-implantation--.
Column 12, Line 14; Delete "FIG. 11B" and insert --FIG. 11C--.
Column 13, Line 21; Delete "sizes)" and insert --sizes--.

Signed and Sealed this
Seventh Day of October, 2014

Michelle K. Lee
*Deputy Director of the United States Patent and Trademark Office*